(12) United States Patent
Lisanti et al.

(10) Patent No.: US 12,319,690 B2
(45) Date of Patent: Jun. 3, 2025

(54) SELECTIVE CDK 4/6 INHIBITOR CANCER THERAPEUTICS

(71) Applicant: LUNELLA BIOTECH, INC., Ottawa (CA)

(72) Inventors: Michael P. Lisanti, Didsbury Village (GB); Federica Sotgia, Didsbury Village (GB); Jussi Kangasmetsa, Cambridge (GB); Luma G. Magalhães, Salford (GB)

(73) Assignee: LUNELLA BIOTECH, INC., Ontario (CA)

( * ) Notice: Subject to any disclaimer, the term of this patent is extended or adjusted under 35 U.S.C. 154(b) by 428 days.

(21) Appl. No.: 17/785,239

(22) PCT Filed: Dec. 15, 2020

(86) PCT No.: PCT/IB2020/061968
§ 371 (c)(1),
(2) Date: Jun. 14, 2022

(87) PCT Pub. No.: WO2021/124104
PCT Pub. Date: Jun. 24, 2021

(65) Prior Publication Data
US 2023/0044749 A1 Feb. 9, 2023

Related U.S. Application Data

(60) Provisional application No. 62/966,834, filed on Jan. 28, 2020, provisional application No. 62/948,498, filed on Dec. 16, 2019.

(51) Int. Cl.
*C07D 471/04* (2006.01)
*A61P 35/00* (2006.01)
*C07D 401/14* (2006.01)
*C07D 487/04* (2006.01)

(52) U.S. Cl.
CPC ............ *C07D 471/04* (2013.01); *A61P 35/00* (2018.01); *C07D 401/14* (2013.01); *C07D 487/04* (2013.01)

(58) Field of Classification Search
CPC .. C07D 471/04; C07D 401/14; C07D 487/04; A61P 35/00; A61P 35/04; A61K 9/20; A61K 31/519
See application file for complete search history.

(56) References Cited

FOREIGN PATENT DOCUMENTS

| CA | 3 096 790 | 10/2019 | |
|---|---|---|---|
| CN | 110357889 A | 10/2019 | |
| WO | WO 03/062236 A1 | 7/2003 | |
| WO | WO 2007/140222 A2 | 12/2007 | |
| WO | WO 2010/020675 A1 | 2/2010 | |
| WO | WO 2011/130232 A1 | 10/2011 | |
| WO | 2017/101763 | 6/2017 | |
| WO | WO-2017101763 A1 * | 6/2017 | ............. A61P 35/02 |
| WO | 2018/106870 | 6/2018 | |

OTHER PUBLICATIONS

Qingxiang Guo et al., "Selective and Novel Cyclin-Dependent Kinases 4 Inhibitor: Synthesis and Biological Evaluation", Medicinal Chemistry Research (2018), No. 27, pp. 1666-1678, https://doi.org/10.1007/s00044-018-2180-2.

International Search Report and Written Opinion of the ISA for PCT/IB2020/061968 dated Mar. 17, 2021, 9 pages.

* cited by examiner

*Primary Examiner* — Matthew P Coughlin
*Assistant Examiner* — Meghan C Heasley
(74) *Attorney, Agent, or Firm* — Nixon & Vanderhye, P.C.

(57) ABSTRACT

The disclosure describes selective and potent CDK 4/6 inhibitors that show advantageous inhibition of cancer growth, even at low concentrations. A class of the CDK 4/6 inhibitors relates to substituted pyridopyrimidines compounds having a fatty acid moiety, and are namely derivatives of Palbociclib of general formula [2A], wherein $R^1$ is hydrogen, aryl, alkyl, alkoxy, cycloalkyl, or heterocyclyl; $R^2$ is hydrogen, halogen, alkyl, acyl, cycloalkyl, alkoxy, alkoxy alkyl, haloalkyl, hydroxy alkyl, alkenyl, alkynyl, nitrile, or nitro; $R^3$ is hydrogen, halogen, alkyl, haloalkyl, hydroxy alkyl, or cycloalkyl; and n is an integer from 9 to 20. These compounds may be used as pharmaceutical compounds for anti-cancer therapies, and are useful for the treatment, prevention and/or amelioration of cancer.

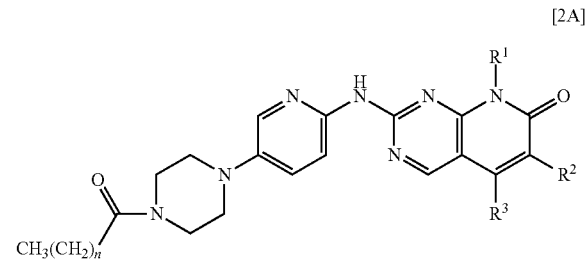

[2A]

15 Claims, 5 Drawing Sheets

SELECTIVE CDK 4/6 INHIBITOR CANCER THERAPEUTICS

CROSS-REFERENCE TO RELATED APPLICATIONS

This application is the U.S. national phase of International Application No. PCT/IB2020/061968 filed Dec. 15, 2020 which designated the U.S. and claims priority to U.S. Provisional Patent Application Nos. 62/948,498 filed Dec. 16, 2019, and 62/966,834 filed Jan. 28, 2020, the entire contents of each of which are hereby incorporated by reference.

FIELD

The present disclosure relates to pharmaceutical compounds for anti-cancer therapies, and more specifically to substituted pyrrolopyrimidine compounds, substituted pyridopyrimidine compounds, and substituted benzimidazole compounds, that as potent CDK 4/6 inhibitors are useful for the treatment, prevention, and/or amelioration of cancer.

BACKGROUND

Cancer stem cells (CSCs) are tumor-initiating cells (TICs) that are resistant to conventional cancer therapies, such as chemo-therapy and radiation treatment. As a consequence, CSCs are responsible for both tumor recurrence and distant metastasis, driving treatment failure and poor clinical outcomes in cancer patients. Therefore, innovative approaches are necessary to understand how to tackle the problem of CSCs. Mechanistically, this may be related to the ability of CSCs to survive and thrive under harsh conditions and different micro-environments. Because CSCs are an especially small sub-set of the tumor cell population, their metabolic and phenotypic properties have remained largely uncharacterized, until recently.

Moreover, CSCs are strikingly resilient and highly resistant to cellular stress, which allows them to undergo anchorage-independent growth, especially under conditions of low-attachment. As a consequence, they form 3D spheroids, which retain the properties of CSCs and stem cell progenitors. In contrast, when subjected to growth in suspension, most "bulk" cancer cells die, via anoikis—a specialized type of apoptosis. As such, the clonal propagation of a single CSC results in the production of a 3D spheroid and does not involve the self-aggregation of cancer cells. Therefore, 3D spheroid formation is a functional read-out for stemness in epithelial cancer cells and allows one to enrich for a population of epithelioid cells with a stem-like phenotype. These 3D spheroids are also known as mammospheres when they are prepared using breast cancer cells, such as MCF7, among others.

Previously, 3D spheroids have been generated from 2 distinct ER(+) cells lines (MCF7 and T47D) and subjected to unbiased label-free proteomics analysis. This work started the analysis of the phenotypic behavior of CSCs at a molecular level. The 3D spheroids were directly compared with monolayers of these cell lines and processed in parallel. This allowed for an identification of the proteomic features that are characteristic of the CSC phenotype in 3D spheroids, relative to monolayers. Based on this molecular analysis, mammospheres were observed to be significantly enriched in mitochondrial proteins. These mitochondrial-related proteins included molecules involved in beta-oxidation and ketone metabolism/re-utilization, mitochondrial biogenesis, electron transport, ADP/ATP exchange/transport, CoQ synthesis and ROS production, as well as the suppression of mitophagy. As such, increased mitochondrial protein synthesis or decreased mitophagy could allow the accumulation of mitochondrial mass in CSCs.

Given the increases in CSCs, mitochondrial mass is being considered as a new metabolic biomarker to purify CSCs. Using this overall approach, it has been observed that it was possible to significantly enrich CSC activity using only MitoTracker, as a single marker for both ER(+) (MCF7) and ER(−) (MDA-MB-231) breast cancer cell lines. Remarkably, MitoTracker-high cells were found to be chemo-resistant to Paclitaxel, exhibiting resistance to the Paclitaxel-induced DNA-damage response.

What is needed, however, are new pharmaceutical compounds for anti-cancer therapies that eradicate CSCs, prevent or reduce the likelihood of metastasis and/or recurrence, and reduce or eliminate cancer resistance to chemotherapies and other anti-cancer therapies. Additionally, what is needed are therapeutic strategies and anti-cancer therapies that specifically target the "fittest" CSCs, and eliminate further cancer growth, including anchorage-independent growth, tumor recurrence, and distant metastasis.

BRIEF SUMMARY

Cancer stem cells (CSCs) are now believed to be one of the main root causes of treatment failure in cancer patients world-wide. Mechanistically, this may be related to the ability of CSCs to survive and thrive under harsh conditions and different micro-environments. The inventors proposed the theory that CSCs might become resistant to conventional therapies by "boosting" ATP production using an elevated mitochondrial OXPHOS metabolism. Consistent with this view, a variety of mitochondrial inhibitors successfully blocked 3D tumor sphere formation, including i) FDA-approved antibiotics (doxycycline, tigecycline, azithromycin, pyrvinium pamoate, atovaquone, bedaquiline), ii) natural compounds (actinonin, CAPE, berberine, brutieridin and melitidin), as well as iii) experimental compounds (oligomycin and AR-C155858, an MCT1/2 inhibitor), among others.

Cyclin-dependent kinases (CDKs) 4 and 6 are enzymes known to promote cell mitosis and meiosis, both in normal cells and in cancer cells. These enzymes are responsible for phosphorylating and thus deactivating the retinoblastoma protein, which plays a role in cell cycle progression from the G1 phase to the S phase. Research has identified abnormalities in cancer cells that increase the activity of CDKs. This increased activity results in an inactivation of various tumor suppressor genes, and thus paves the way for rapid cancer stem cell proliferation and tumor growth. Naturally occurring protein inhibitors of CDKs, such as p16 and p27, have been shown to inhibit growth in vitro of lung cancer cell lines. Certain CDK inhibitors may be useful as chemoprotective agents through their ability to inhibit cell cycle progression of normal untransformed cells.

Targeted inhibition of these enzymes is one potential strategy for anti-cancer treatments and therapeutics, either alone or in combination with other therapies. Blocking the CDK 4/6 pathway prevents cells from progressing to the S phase, which effectuates cell death via apoptosis. Described herein are three classes of CDK inhibitors, and primarily inhibitors of CDK 4 and CDK 6 ("CDK 4/6"), that have strong efficacy as cancer therapeutics. The first class of anti-cancer CDK 4/6 inhibitors are substituted pyrrolopyrimidine compounds having a fatty acid moiety. The formula shown below, in which 'n' is an integer from 9-20, and more preferably from 12-20, is illustrative of some embodiments in the first class of anti-cancer CDK 4/6 inhibitors.

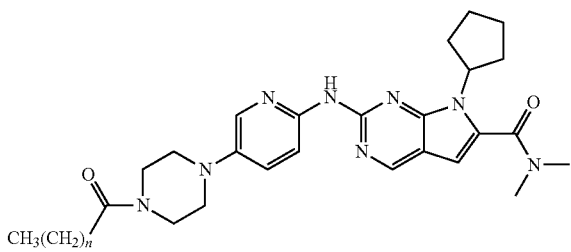

The second class comprises substituted pyridopyrimidines, having a fatty acid moiety. The formula shown below, in which 'n' is an integer from 9-20, and more preferably from 12-20, is illustrative of embodiments in the second class of anti-cancer CDK 4/6 inhibitors.

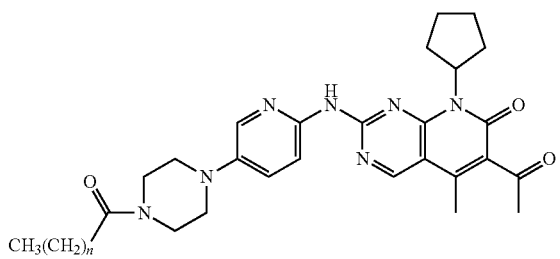

The third class comprises substituted benzimidazole compounds, having a fatty acid moiety. The formula shown below, in which 'm' is an integer from 0-4, and more preferably 0-2, and 'n' is an integer from 9-20, and more preferably from 12-20, is illustrative of embodiments in the third class of anti-cancer CDK 4/6 inhibitors.

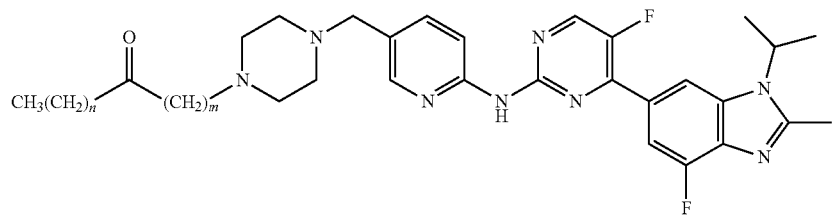

Compounds in either the first class, second class, or third class, including salts thereof, may be used as a pharmaceutical compound for the treatment of cancer. Demonstrative salts include succinate, trifluoroacetate, tartrate, and malate, among others as will be appreciated by those having an ordinary level of skill in the art. The present approach also provides pharmaceutical formulations having a therapeutically effective amount of a compound from either the first class, the second class, or the third class, or in some embodiments one or more from each class, or a therapeutically acceptable salt(s) thereof, and a pharmaceutically acceptable carrier, diluent, or excipient therefor. All of these forms are within the present approach. It should be appreciated that a pharmaceutically acceptable carrier, as are known in the art, may be used.

Compounds described herein may be used in connection with methods of treating cancer, in a mammal, including humans, comprising administering to the mammal an amount of a compound from either the first class, the second class, or the third class, or a pharmaceutically acceptable salt thereof, which is effective in treating such disorder or condition. For example, the present approach is useful for treating abnormal cell proliferation such a cancer. The compounds described herein may be used for treating the abnormal cell proliferation disorders, and in particular a cancer selected from the group consisting of cancers of the breast, ovary, cervix, prostate, testis, esophagus, stomach, skin, lung, bone, colon, pancreas, thyroid, biliary passages, buccal cavity and pharynx (oral), lip, tongue, mouth, pharynx, small intestine, colon-rectum, large intestine, rectum, brain and central nervous system, glioblastoma, neuroblastoma, keratoacanthoma, epidermoid carcinoma, large cell carcinoma, adenocarcinoma, adenocarcinoma, adenoma, adenocarcinoma, follicular carcinoma, undifferentiated carcinoma, papillary carcinoma, seminoma, melanoma, sarcoma, bladder carcinoma, liver carcinoma, kidney carcinoma, myeloid disorders, lymphoid disorders, Hodgkin's, hairy cells, and leukemia, by administering a therapeutically effective amount of a compound from the first class, the second class, or the third class, or a pharmaceutically acceptable salt thereof, to a subject having been diagnosed with such a cancer. In some embodiments, the present approach may be used in combination with, and/or to increase the effectiveness of, other therapies.

Some embodiments of the present approach may take the form of a compound having the general formula

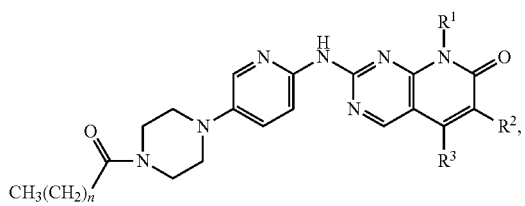

in which:

$R^1$ is hydrogen, aryl, $C_1$-$C_8$ alkyl, $C_1$-$C_8$ alkoxy, $C_3$-$C_7$ cycloalkyl, or $C_3$-$C_7$-heterocyclyl;

$R^2$ is independently selected from hydrogen, halogen, $C_1$-$C_8$ alkyl, $C_1$-$C_8$ acyl, $C_3$-$C_7$ cycloalkyl, $C_1$-$C_8$ alkoxy, $C_1$-$C_8$ alkoxyalkyl, $C_1$-$C_8$ haloalkyl, $C_1$-$C_8$ hydroxyalkyl, $C_2$-$C_8$ alkenyl, $C_2$-$C_8$ alkynyl, nitrile, nitro, $OR^5$, $SR^5$, $NR^5R^6$, $N(O)R^5R^6$, $P(O)(OR^5)(OR^6)$, $(CR^5R^6)_m NR^7R^8$, $COR^5$, $(CR^4R^5)_m C(O)R^7$, $CO_2R^5$, $CONR^5R^6$, $C(O)NR^5SO_2R^6$, $NR^5SO_2R^6$, $C(O)NR^5OR^6$, $S(O)_n R^5$, $SO_2NR^5R^6$, $P(O)(OR^5)(OR^6)$, $(CR^5R^6)_m P(O)(OR^7)(OR^8)$, $(CR^5R^6)_m$-aryl, $(CR^5R^6)_m$-heteroaryl, and —$CR^5R^6C(O)R^7$;

$R^3$ is, in each instance, independently, hydrogen, halogen, $C_1$-$C_6$ alkyl, $C_1$-$C_6$ haloalkyl, $C_1$-$C_6$ hydroxyalkyl, or $C_3$-$C_7$ cycloalkyl;

$R^{5'}$ $R^6$, $R^7$, and $R^8$, are independently are hydrogen, $C_1$-$C_8$ alkyl, $C_2$-$C_8$ alkenyl, $C_2$-$C_8$ alkynyl, arylalkyl, cycloalkyl, heterocycloalkyl, aryl, heteroaryl, or heteroarylalkyl; m is from 0 to 6; and n represents an integer from 9 to 20, and preferably, from 12 to 20. In some preferred embodiments, $R^1$ is cyclopentyl, and $R^2$ is acetyl. Further, in some embodiments, n is preferably 12.

In some embodiments, the present approach may take the form of a pharmaceutical composition including a compound as described herein as the active therapeutic agent, or a pharmaceutically acceptable salt thereof, and a pharmaceutically acceptable carrier. For example, the composition may be, in some embodiments, a tablet having a core with between 18% and 55% by weight of the active therapeutic agent, and a pharmaceutically acceptable carrier. The pharmaceutically acceptable carrier may be, for instance, microcrystalline cellulose, crospovidone type A, low-substituted hydroxypropylcellulose, magnesium stearate, and colloidal anhydrous silica.

The compounds and pharmaceutical compositions described herein have a potency and selectivity towards cancer stem cells that renders them suitable for various anti-cancer therapeutic uses. For example, the present approach may take the form of methods for preventing or reducing the proliferation of at least one of cancer cells, cancer stem cells, and circulating tumor cells, in which a patient in need thereof is administered a pharmaceutically effective amount of a compound or pharmaceutical composition as described herein.

The present approach may take the form of methods for treating cancer, in which a patient in need thereof is administered a pharmaceutically effective amount of a compound or pharmaceutical composition as described herein.

The present approach may take the form of methods for treating or preventing metastatic diseases, in which a patient in need thereof is administered a pharmaceutically effective amount of a compound or pharmaceutical composition as described herein.

The present approach may take the form of methods for treating or preventing tumor recurrence, in which a patient in need thereof is administered a pharmaceutically effective amount of a compound or pharmaceutical composition as described herein.

The present approach may take the form of methods for reducing the treatment resistance of a cancer, such as chemotherapy resistance, in which a patient in need thereof is administered a pharmaceutically effective amount of a compound or pharmaceutical composition as described herein.

The present approach may take the form of methods for t treating or preventing at least one of radiation therapy resistance, chemotherapy resistance, and hormone therapy resistance, in which a patient in need thereof is administered a pharmaceutically effective amount of a compound or pharmaceutical composition as described herein.

It should be appreciated that the person having an ordinary level of skill in the art may apply common methods known in the art to determine the treatment dosage, dosage form, and dosing schedule for a particular embodiment.

The compounds of the present approach may also be used in the manufacture of a medicament for a number of therapeutic uses, such as the treatment or prevention of cancer, the treatment or prevention of metastatic disease, and the treatment or prevention of tumor recurrence.

Embodiments of the present approach may be recognized by those having ordinary skill in the art, having reviewed the following detailed description.

DRAWINGS

DESCRIPTION

Figure 1:
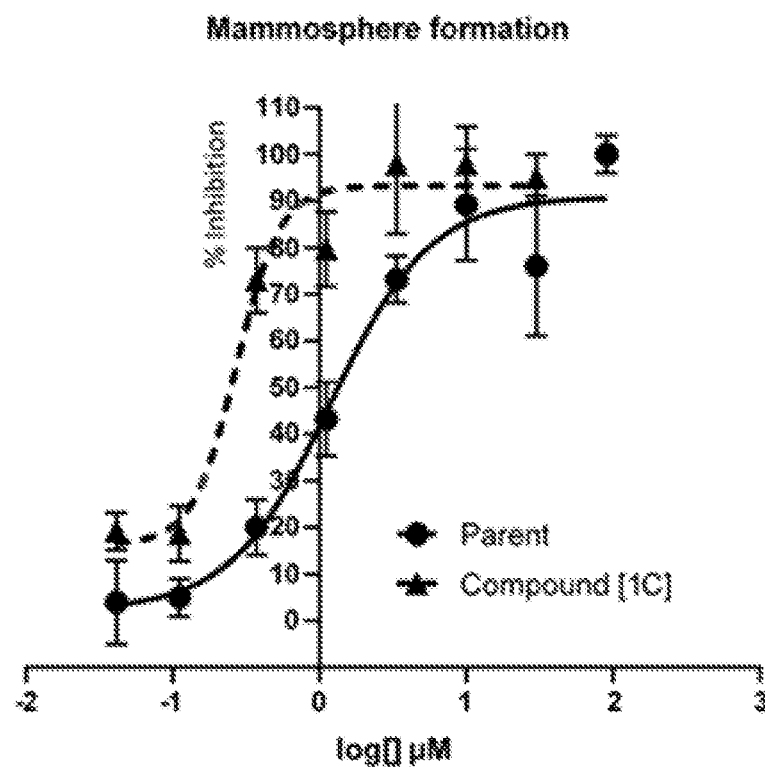
FIG. 1 shows dose-response curves comparing Compound [1C] to its parent compound, using the mammosphere formation assay on the MCF7 cell line.

The following description includes the currently contemplated modes of carrying out exemplary embodiments of the present approach. The following description is not to be taken in a limiting sense, and is made merely for the purpose of illustrating the general principles of the invention.

Under the present approach, compounds from three classes of CDK 4/6 inhibitors may be used as anti-cancer therapeutics. The first class comprises substituted pyrrolopyrimidine compounds having a fatty acid moiety. The second class comprises substituted pyridopyrimidine compounds having a fatty acid moiety. The third class comprises substituted benzimidazole compounds having a fatty acid moiety. The compounds described herein have useful pharmaceutical and medicinal properties. Many of the compounds exhibit significant selective CDK 4/6 inhibitory activity and therefore are of value in the treatment of a wide variety of clinical conditions in which CDK 4/6 kinases are abnormally elevated, or activated or present in normal amounts and activities, but where inhibition of the CDKs is desirable to treat a cellular proliferative disorder. In particular, these compounds are promising as anti-cancer therapeutics. Compounds in each class are described below the following definitions, which are applicable to embodiments of the present approach.

As used herein, the notation C(O) refers to a carbon to oxygen double bond. The term "halo" used herein means a halogen, and includes fluorine, chlorine, bromine, or iodine, bonded as is understood in the art.

The term "alkyl" used herein refers to saturated aliphatic groups, including straight-chain alkyl groups (e.g., methyl, ethyl, etc.), branched-chain alkyl groups (isopropyl, tert-butyl, etc.), cycloalkyl (alicyclic) groups (cyclopropyl, cyclopentyl, cyclohexyl, cycloheptyl, cyclooctyl), alkyl-substituted cycloalkyl groups, and cycloalkyl substituted alkyl groups. The term "alkyl" also includes alkenyl groups and alkynyl groups. General formula may use the term "$C_n$-alkyl", wherein n is an integer from, e.g., 1-20, to indicate a particular alkyl group (straight- or branched-chain) of a particular range or number of carbons in the group. For example, the term $C_1$-$C_3$-alkyl includes, but is not limited to, methyl, ethyl, propyl, and isopropyl. Similarly, the term $C_{3-6}$-cycloalkyl includes, but is not limited to, cyclopropyl, cyclopentyl, and cyclohexyl. Alkyl groups, as well as cycloalkyl groups, may be unsubstituted or substituted. Thus, the term alkyl includes both "unsubstituted alkyl" and "substituted alkyl", the latter of which refers to moieties having substituents replacing a hydrogen on one or more carbons of the hydrocarbon backbone.

The term "alkenyl" includes unsaturated aliphatic groups analogous in length and possible substitution to the alkyls described above, but which contain at least one double bond. Alkenyl also include "unsubstituted alkenyls" and "substituted alkenyls," the latter of which refers to moieties having substituents replacing a hydrogen on one or more carbons of the hydrocarbon backbone.

For example, the term "alkenyl" includes straight-chain alkenyl groups (e.g., ethenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups that include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

The term "alkynyl" includes unsaturated aliphatic groups analogous in length and possible substitution to the alkyls described above, but which contain at least one triple bond. Moreover, the term alkynyl includes both "unsubstituted alkynyls" and "substituted alkynyls," the latter of which refers to alkynyl moieties having substituents replacing a hydrogen on one or more carbons of the hydrocarbon backbone.

As examples, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups that include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

The term "substituted" is intended to describe moieties having substituents replacing a hydrogen on one or more atoms, e.g. C, O or N, of a molecule. Such substituents can include, for example but not limited to, alkyl, alkoxy, alkenyl, alkynyl, halo, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, morpholino, phenol, benzyl, phenyl, piperizine, cyclopentane, cyclohexane, pyridine, 5H-tetrazole, triazole, piperidine, or an aromatic or heteroaromatic moiety, and combinations thereof.

The terms "amine" or "amino" should be refer to both a molecule, or a moiety or functional group, as generally understood in the art, and may be primary, secondary, or tertiary. The term "amine" or "amino" includes compounds where a nitrogen atom is covalently bonded to at least one carbon, hydrogen or heteroatom. The terms include, for example, but are not limited to, "alkylamino," "arylamino," "diarylamino," "alkyl aryl amino," "alkylaminoaryl," "arylaminoalkyl," "alkaminoalkyl," "amide," "amido," and "aminocarbonyl." The term "alkyl amino" comprises groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide," "amido" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

The term "aryl" includes groups, including 5- and 6-membered single-ring aromatic groups that may include from zero to four heteroatoms, for example, phenyl, pyrrole, furan, thiophene, thiazole, isothiaozole, imidazole, triazole, tetrazole, pyrazole, oxazole, isoxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, anthryl, phenanthryl, naphthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics." The aromatic ring can be substituted at one or more ring positions with such substituents as described above, as for example, alkyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrahydro analogs thereof. Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

The term "acyl" includes compounds and moieties which contain the acyl radical (CH3CO—) or a carbonyl group. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups and may include cyclic groups such as cyclopentoxy. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "carbonyl" or "carboxy" includes compounds and moieties which contain a carbon connected with a double bond to an oxygen atom, and tautomeric forms thereof. Examples of moieties that contain a carbonyl include aldehydes, ketones, carboxylic acids, amides, esters, anhydrides, etc. The term "carboxy moiety" or "carbonyl moiety" refers to groups such as "alkylcarbonyl" groups wherein an alkyl group is covalently bound to a carbonyl group, "alkenylcarbonyl" groups wherein an alkenyl group is covalently bound to a carbonyl group, "alkynylcarbonyl" groups wherein an alkynyl group is covalently bound to a carbonyl group, "arylcarbonyl" groups wherein an aryl group is covalently attached to the carbonyl group. Furthermore, the term also refers to groups wherein one or more heteroatoms are covalently bonded to the carbonyl moiety.

For example, the term includes moieties such as, for example, aminocarbonyl moieties, (wherein a nitrogen atom is bound to the carbon of the carbonyl group, e.g., an amide), aminocarbonyloxy moieties, wherein an oxygen and a nitrogen atom are both bond to the carbon of the carbonyl group (e.g., also referred to as a "carbamate"). Furthermore, aminocarbonylamino groups (e.g., ureas) are also include as well as other combinations of carbonyl groups bound to heteroatoms (e.g., nitrogen, oxygen, sulfur, etc. as well as carbon atoms). Furthermore, the heteroatom can be further substituted with one or more alkyl, alkenyl, alkynyl, aryl, aralkyl, acyl, etc. moieties.

The term "thiocarbonyl" or "thiocarboxy" includes compounds and moieties which contain a carbon connected with a double bond to a sulfur atom. The term "thiocarbonyl moiety" includes moieties that are analogous to carbonyl moieties. For example, "thiocarbonyl" moieties include aminothiocarbonyl, wherein an amino group is bound to the carbon atom of the thiocarbonyl group, furthermore other thiocarbonyl moieties include, oxythiocarbonyls (oxygen bound to the carbon atom), aminothiocarbonylamino groups, etc.

The term "ether" includes compounds or moieties that contain an oxygen bonded to two different carbon atoms or heteroatoms. For example, the term includes "alkoxyalkyl" which refers to an alkyl, alkenyl, or alkynyl group covalently bonded to an oxygen atom that is covalently bonded to another alkyl group.

The term "ester" includes compounds and moieties that contain a carbon or a heteroatom bound to an oxygen atom that is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom that is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O—.

The terms "polycyclyl" or "polycyclic radical" include moieties with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

Additionally, the phrase "any combination thereof" implies that any number of the listed functional groups and molecules may be combined to create a larger molecular architecture. For example, the terms "phenyl," "carbonyl" (or "=O"), "—O—," "—OH," and $C_{1-6}$ (i.e., —CH$_3$ and —CH$_2$CH$_2$CH$_2$—) can be combined to form a 3-methoxy-4-propoxybenzoic acid substituent. It is to be understood that when combining functional groups and molecules to create a larger molecular architecture, hydrogens can be removed or added, as required to satisfy the valence of each atom.

The compounds described herein include bonds between adjacent atoms and/or hydrogens as required to satisfy the valence of each atom, as would be understand by those having an ordinary level of skill in the art. Bonds and/or hydrogen atoms are added, if necessary, to provide the following number of total bonds to each of the following types of atoms: carbon: four bonds; nitrogen: three bonds; oxygen: two bonds; and sulfur: two-six bonds.

The term "salt" of a compound relates to corresponding salt prepared by using acid selected from the group of mineral acids, such as hydrochloric acid, hydrobromic acid, phosphoric acid, metaphosphoric acid, nitric acid and sulphuric acid, and organic acids, such as tartaric acid, acetic acid, trifluoroacetic acid, citric acid, malic acid, lactic acid, fumaric acid, benzoic acid, glycolic acid, gluconic acid and succinic acid, and alkylsulphonic acids such as methanesulphonic, ethanesulphonic acids, ethane-1,2-disulfonic acid and 2-hydroxyethanesulfonic acid and arylsulphonic acids such as benzene sulfonic acid, 2-naphthalenesulfonic acid, p-toluenesulphonic acid and naphthalene-1,5-disulfonic acid.

The phrase, "pharmaceutically effective amount" as used herein indicates an amount necessary to administer to a host, or to a cell, tissue, or organ of a host, to achieve a therapeutic result, such as the regulating, modulating, or inhibiting protein kinase activity, e.g., inhibition of the activity of a protein kinase, or treatment of cancer. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. For example, common and known methods in the art may be used to establish both the maximum tolerable dose of a compound, and the effective dose that provides a detectable therapeutic benefit to a person in need thereof. Likewise, common and known methods in the art may be used to determine the dosage and dosing schedule for administering the therapeutic agent sufficient to provide a detectable therapeutic benefit. The demonstrative dosing examples disclosed herein in no way limit the potential dosage and dosing schedules that may be provided under the present approach.

The term "about" means having a value falling within an accepted standard of error of the mean, when considered by one of ordinary skill in the art. As would be expected, the meaning of "about" depends on the context in which it is used. Frequently, the term "about" may refer to ±5%, and preferably ±2.5%, and more preferably ±1% of the value or range to which it refers. For example, in the context of weight fractions, the phrase "about 20%" may mean 20%±5%, preferably 20%±2.5%, and more preferably 20%±1%.

The terms "treat," "treated," "treating," and "treatment" include the diminishment or alleviation of at least one symptom associated or caused by the state, disorder or disease being treated, in particular, cancer. In certain embodiments, the treatment comprises diminishing and/or alleviating at least one symptom associated with or caused by the cancer being treated, by the compound of the invention. For example, treatment can be diminishment of one or several symptoms of a cancer or complete eradication of a cancer.

The compounds described herein include what this disclosure refers to as a fatty acid moiety. As used herein, a fatty acid is a carboxylic acid with an aliphatic chain, which may be saturated or unsaturated, although saturated chains are preferred. Examples of saturated fatty acids include lauric acid ($CH_3(CH_2)_{10}COOH$), palmitic acid ($CH_3(CH_2)_{14}COOH$), stearic acid ($CH_3(CH_2)_{16}COOH$), and myristic acid ($CH_3(CH_2)_{12}COOH$). Oleic acid ($CH_3(CH_2)_7CH=CH(CH_2)_7COOH$) is an example of a naturally occurring unsaturated fatty acid. References may also be made to the salt or ester of a fatty acid, as well as its fatty amide moiety, but for simplicity these are included in the meaning of fatty acid moiety as used herein. For example, myristic acid may be referred to as myristate, and oleic acid may be referred to as oleate. A fatty acid moiety may also be a carboacyl of the fatty acid, i.e., a group formed by the loss of a hydroxide group of a carboxylic acid. In some embodiments, a fatty acid moiety may be bonded to a therapeutic agent through an amide bond. As an example, a myristic acid conjugate may have a fatty acid moiety $CH_3(CH_2)_{12}CO-NH-$, where the tertiary nitrogen is bonded to the therapeutic agent:

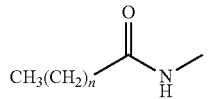

and n is an integer from 1 to 20, and is preferably 10 to 20. This may result when the myristate moiety is conjugated through myristoylation, resulting in a tetradecanamide (or myristamide) group.

Substituted Pyrrolopyrimidine Compounds

In some embodiments of the present approach, a first class of anti-cancer CDK 4/6 inhibitors are substituted pyrrolopyrimidine compounds, and pharmaceutically acceptable salts thereof. It should be appreciated that some compounds in the first class are derivatives of parent compound 7-cyclopentyl-N,N-dimethyl-2-[(5-piperazin-1-ylpyridin-2-yl)amino]pyrrolo[2,3-d]pyrimidine-6-carboxamide, also known as Ribociclib. Some embodiments in the first class have the chemical structure shown in general formula [1A], below, in which a fatty acid moiety is bonded to the piperazine.

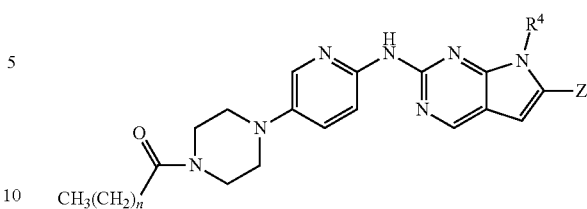

As used in general formula [1A]:

$R^4$ is selected from the group consisting of hydrogen, $C_1$-$C_8$-alkyl, substituted $C_1$-$C_8$-alkyl, $C_3$-$C_8$-cycloalkyl, substituted $C_3$-$C_8$-cycloalkyl, aryl, substituted aryl, heteroaryl and substituted heteroaryl;

Z is $CR^z$ in which $R^z$ is selected from the group consisting of halo, hydrogen, $C_1$-$C_3$-alkyl, $C_1$-$C_3$-alkoxy, CN, C=NOH, C=NOCH$_3$, C(O)H, C(O)C$_1$-C$_3$-alkyl, C$_3$-C$_8$-cycloalkyl, heterocyclyl, aryl, heteroaryl, substituted $C_1$-$C_3$-alkyl, substituted $C_3$-$C_8$-cycloalkyl, substituted heterocyclyl, substituted aryl, substituted heteroaryl, —B—NR$^a$R$^b$, —B—OR$^a$, —B—C(O)R$^a$, —B—C(O)OR$^a$, —B—C(O)NR$^a$R$^a$; wherein B is either a bond, a $C_1$-$C_3$-alkyl, or a branched $C_1$-$C_3$-alkyl; and $R^a$ and $R^b$ are each, independently, selected from the group consisting of hydrogen, $C_1$-$C_3$-alkyl, $C_3$-$C_8$-cycloalkyl, heterocyclyl, aryl, heteroaryl, substituted alkyl, substituted cycloalkyl, substituted heterocyclyl, substituted aryl, and substituted heteroaryl; and in the fatty acid moiety, 'n' represents an integer from 9 to 20, and is preferably from 12-20.

It should be appreciated that pharmaceutically acceptable salts may also be used. As referenced above, salts may be prepared through using an acid selected from mineral acids, organic acids, alkylsulphonic acids, ethanesulphonic acids, and arylsulphonic acids, for example. In some preferred embodiments of the present approach, a first class of anti-cancer CDK 4/6 inhibitors are compounds having the general formula [1B] shown below. In such embodiments, $R^4$ is a $C_5$-cycloalkyl, Z is a dimethyl carboxamide or acetyl, and n represents an integer from 9 to 20, and more preferably from 12-20. This general formula's parent compound is Ribociclib, an FDA-approved pharmaceutical used to treat HR-positive, HER2-negative advanced or metastatic breast cancers (with an aromatase inhibitor). However, embodiments of the present approach according to formula 1[A] have a $C_{11}$-$C_{22}$ fatty acid moiety conjugated at the terminal piperazine. Preferably, the fatty acid moiety is linear and saturated. In some preferred embodiments, the fatty acid moiety is one of lauric acid, myristic acid, palmitic acid, and stearic acid. The fatty acid moiety significantly improves the cellular uptake of the compound, greatly increasing its inhibition of cancer stem cell proliferation, and selectivity for tumor cells.

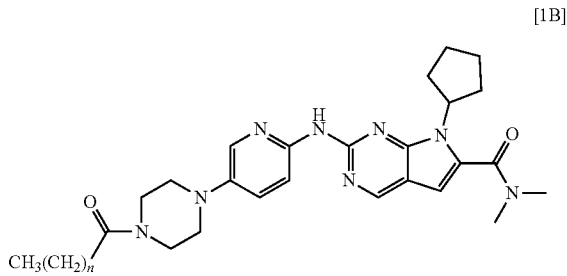

[1B]

A demonstrative embodiment is shown below as Compound [1C], in which $R^4$ is unsubstituted $C_5$-cycloalkyl, Z is a dimethyl carboxamide, and n is 12. As a result, this embodiment has a 14-carbon fatty acid (i.e., myristate) moiety. The compound shown as Compound [1C] has been synthesized and, in the mammosphere assay, showed remarkably improved inhibition of MCF7 cells compared to known anti-cancer therapeutic Ribociclib at concentrations from 1 μM to 100 μM, demonstrating the incredible impact the fatty acid moiety has on the compound. In preliminary laboratory evaluations, this embodiment inhibited effectively 100% of cell propagation at concentrations as low as 1 μM, demonstrating superb anti-cancer efficacy. For example, FIG. 1 shows dose-response curves for Compound [1C] and its parent compound, and illustrates the improved CSC inhibition resulting from the addition of the fatty acid moiety. It should be appreciated that similar results are expected for other fatty acid moieties having as few as 11 carbons and as many as 22 carbons.

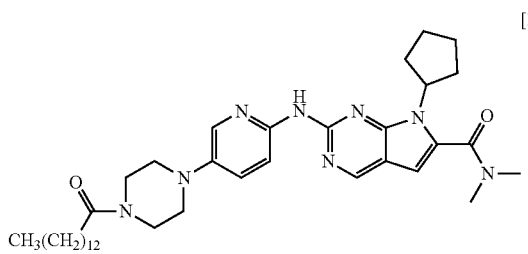

[1C]

In some embodiments of the present approach, a first class of anti-cancer CDK 4/6 inhibitors are substituted pyrrolopyrimidine compounds as shown below in general formula [1D]. As compared to the general formula [1A], compounds having the general formula [1D] include a fatty acid moiety at Z. It should be appreciated that pharmaceutically acceptable salts may also be used.

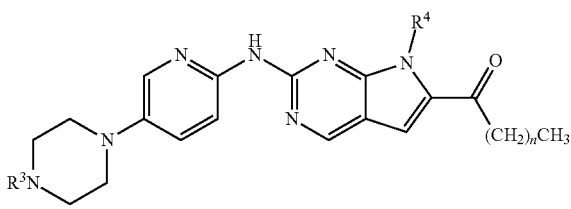

[1D]

As used in general formula [1D]:

$R^4$ is selected from the group consisting of hydrogen, $C_1$-$C_8$-alkyl, substituted $C_1$-$C_8$-alkyl, $C_3$-$C_8$-cycloalkyl, substituted $C_3$-$C_8$-cycloalkyl, aryl, substituted aryl, heteroaryl and substituted heteroaryl;

$R^3$ is selected from the group consisting of hydrogen, OH, $C_1$-$C_8$-alkyl, substituted $C_1$-$C_8$-alkyl, $C_3$-$C_8$-cycloalkyl, C(O) $C_1$-$C_8$-alkyl, $C_1$-$C_8$-haloalkyl, $C_1$-$C_8$-cyanoalkyl, $C_1$-$C_8$-alkyl-OH, $SO_2$—$C_1$-$C_8$-alkyl, $C_1$-$C_6$-alkyl-$C_3$-$C_8$-cycloalkyl, and $C_1$-$C_8$-alkoxy, which may be substituted or unsubstituted when $R^3$ is not hydrogen; and in the fatty acid moiety, 'n' represents an integer from 9 to 20, and is preferably from 12-20.

In preferred embodiments of the present approach, a first class of anti-cancer CDK 4/6 inhibitors are compounds having the general formula [1E] shown below. In such embodiments, $R^4$ is a $C_5$-cycloalkyl, $R^3$ is hydrogen, and n represents an integer from 9 to 20, and more preferably from 10-20, and more preferably from 10-16. Compounds having the general formula [1E] are derivatives of Ribociclib, in which a fatty acid moiety replaces the dimethyl-amino group at the carboxyl.

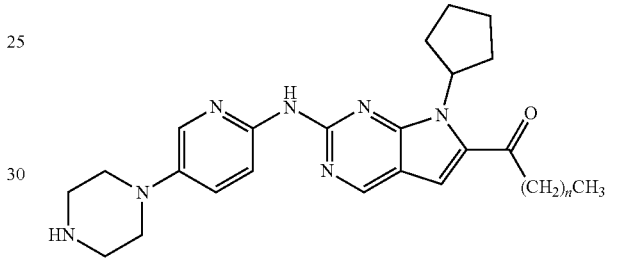

[1E]

A demonstrative embodiment is shown below formulas Compound [1F], in which $R^4$ is unsubstituted $C_5$-cycloalkyl, $R^3$ is hydrogen, and n is 12. As a result, this embodiment has a 14-carbon fatty acid (i.e., myristate) moiety. Compound [1F] is expected to show improved inhibition in the mammosphere assay.

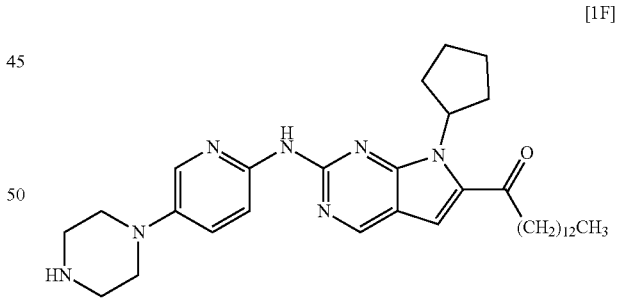

[1F]

Table 1, below, summarizes results for various assays comparing Compound [1C] and its parent compound (Ribociclib), and contains the in vitro biological data for both compounds. Compound [1C] showed a 7-fold improvement in potency in the 3D-mammosphere assay ($IC_{50}$ of about 0.2 vs. about 1.5 μM), when compared to the parent compound, while retaining similar activity in the 2D-cell viability assay ($IC_{50}$ of about 2 μM for both compounds). This demonstrates that the conjugation with a fatty acid moiety greatly improving not only the potency in the 3D-mammosphere assay. Comparing the mammosphere-monolayer selectivity indices ("SI") shows that the conjugation also improves the selectivity towards the mammospheres (SI 10 vs. 1.3). Both compounds where non-toxic in the non-tumoral cell line hTERT-BJ1 up to the concentration of 90 μM, representing high selectivity towards the tumor cell line. As can be seen, compounds according to the present approach result in significantly improved potency and selectivity towards tumor cells.

TABLE 1

Mammosphere assay results for demonstrative compound in first class.

| Compound | $IC_{50}$ (MCF7 mammosphere) | $IC_{50}$ (MCF7 monolayer) | SI (mammosphere/monolayer MCF7) | $IC_{50}$ (BJ1 monolayer) | SI (BJ1/MCF7 monolayer) |
|---|---|---|---|---|---|
| Ribociclib | 1.5 ± 1.0 μM | 2.0 ± 0.7 μM | 1.3 | >90 μM | >45 |
| Compound [1C] | 0.2 ± 0.1 μM | 2.0 ± 1.0 μM | 10 | >90 μM | >45 |

As used in the tables, "$IC_{50}$ (MCF7 mammosphere)" refers to the half maximal inhibitory concentration in the 3D-mammosphere assay, using the ER+ breast cancer cell line, MCF7. The term "$IC_{50}$ (MCF7 monolayer)" refers to the half maximal inhibitory concentration in the 2D-cell viability assay, using the ER+ breast cancer cell line, MCF7. The term "$IC_{50}$ (BJ1 monolayer)" refers to the half maximal inhibitory concentration in the 2D-cell viability assay, using the immortalized non-tumoral fibroblast cell line, hTERT-BJ1. The term "SI (mammosphere/monolayer MCF7)" refers to the mammosphere selectivity index, a ratio between $IC_{50}$ values comparing the biological activity in the 3D and 2D assays against MCF7. The term "SI (BJ1/MCF7 monolayer)" refers to the cancer selectivity index, a ratio between $IC_{50}$ values comparing the biological activity in the cell viability assays against MCF7 and hTERT-BJ1.

Substituted Pyridopyrimidine Compounds

The second class comprises substituted pyridopyrimidines, having a fatty acid moiety, as shown in general formula [2A] below. It should be appreciated that some embodiments in the second class comprise derivatives of 6-acetyl-8-cyclopentyl-5-methyl-2-(5-piperazin-1-yl-pyridin-2-ylamino)-8H-pyrido[2,3-d]pyrimidin-7-one, also known as Palbociclib. It should also be appreciated that pharmaceutically acceptable salts may also be used, such as those identified above, as would be understood by those having an ordinary level of skill in the art. Other example salts include malate, tartate, bromide, hydrogen bromide dihydrate, hydrogen chloride, sulphate dihydrate, camsylate, napsylate, napsylate dihydrate, tosylate, citrate monohydrate, maleate, and oxalate.

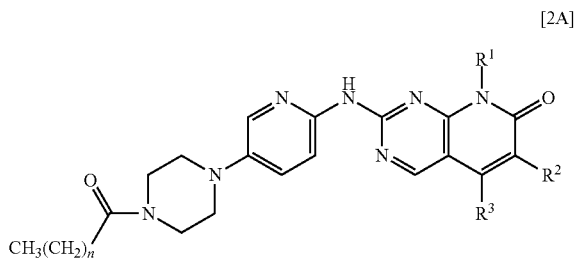

[2A]

In general formula 2[A]:

$R^1$ is hydrogen, aryl, $C_1$-$C_8$ alkyl, $C_1$-$C_8$ alkoxy, $C_3$-$C_7$ cycloalkyl, or $C_3$-$C_7$-heterocyclyl;

$R^2$ is independently selected from hydrogen, halogen, $C_1$-$C_8$ alkyl, $C_1$-$C_8$ acyl, $C_3$-$C_7$ cycloalkyl, $C_1$-$C_8$ alkoxy, $C_1$-$C_8$ alkoxyalkyl, $C_1$-$C_8$ haloalkyl, $C_1$-$C_8$ hydroxyalkyl, $C_2$-$C_8$ alkenyl, $C_2$-$C_8$ alkynyl, nitrile, nitro, $OR^5$, $SR^5$, $NR^5R^6$, $N(O)R^5R^6$, $P(O)(OR^5)(OR^6)$, $(CR^5R^6)_m NR^7R^8$, $COR^5$, $(CR^4R^5)_m C(O)R^7$, $CO_2R^5$, $CONR^5R^6$, $C(O)NR^5SO_2R^6$, $NR^5SO_2R^6$, $C(O)NR^5OR^6$, $S(O)_n R^5$, $SO_2NR^5R^6$, $P(O)(OR^5)(OR^6)$, $(CR^5R^6)_m P(O)(OR^7)(OR^8)$, $(CR^5R^6)_m$-aryl, $(CR^5R^6)_m$-heteroaryl, and $-CR^5R^6C(O)R^7$;

$R^3$ is, in each instance, independently, hydrogen, halogen, $C_1$-$C_6$ alkyl, $C_1$-$C_6$ haloalkyl, $C_1$-$C_6$ hydroxyalkyl, or $C_3$-$C_7$ cycloalkyl;

$R^5$, $R^6$, $R^7$, and $R^8$, are independently are hydrogen, $C_1$-$C_8$ alkyl, $C_2$-$C_8$ alkenyl, $C_2$-$C_8$ alkynyl, arylalkyl, cycloalkyl, heterocycloalkyl, aryl, heteroaryl, or heteroarylalkyl; m is from 0 to 6; and in the fatty acid moiety, n represents an integer from 9 to 20, and preferably is from 12-20.

Shown below as general formula [2B] is a general formula for preferred embodiments of the second class according to the present approach. In general formula [2B], $R^1$ is unsubstituted $C_5$-cycloalkyl, $R^2$ is $C_1$-acyl (acetyl), $R^3$ is methyl, and n represents an integer from 9 to 20, and more preferably from 12-20.

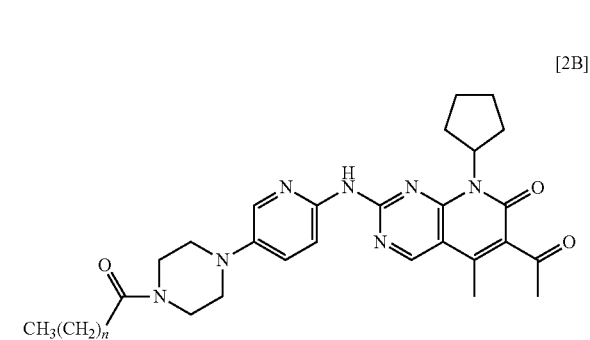

[2B]

Figure 2:
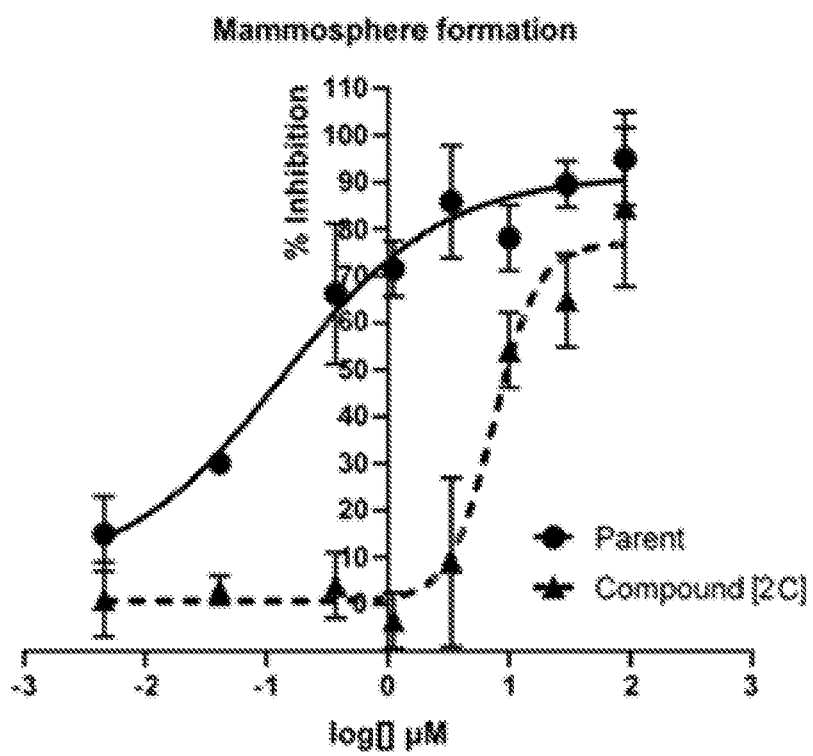
FIG. 2 are dose-response curves comparing Compound [2C] to its parent compound, using the mammosphere formation assay on the MCF7 cell line.

A demonstrative embodiment of the second class is shown below formulas Compound [2C], in which $R^1$ is unsubstituted $C_6$-cycloalkyl, $R^2$ is $C_1$-acyl (acetyl), $R^3$ is methyl, and n 12. As a result, this embodiment has a 14-carbon fatty acid (i.e., myristate) moiety. Compound [2C] has been synthesized and, in the mammosphere assay, showed remarkably improved inhibition of MCF7 cells compared to known anti-cancer therapeutic Palbociclib at concentrations from 1 μM to 100 μM. These results also show that, for the second class of compounds according to the present approach, the fatty acid moiety has a significant beneficial impact on the compound's anti-cancer efficacy. For example, FIG. 2 shows dose-response curves for Compound [2C] and its parent compound, and illustrates the improved CSC inhibition resulting from the addition of the fatty acid moiety. It should be appreciated that similar results are expected for other fatty acid moieties having as few as 11 carbons and as many as 22 carbons.

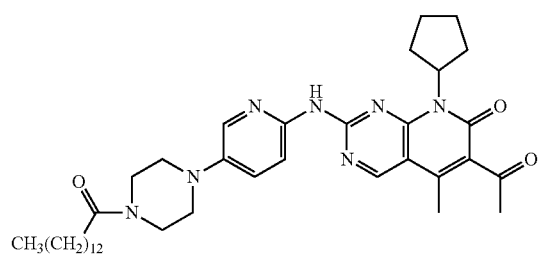

[2C]

The second class also comprises substituted pyridopyrimidines, having a fatty acid moiety, as shown in general formula [2D] below. As can be seen, the fatty acid moiety in formula [2D] is conjugated at the pyrido[2,3-d]pyrimidine, as opposed to the piperazine as seen in formula [2A].

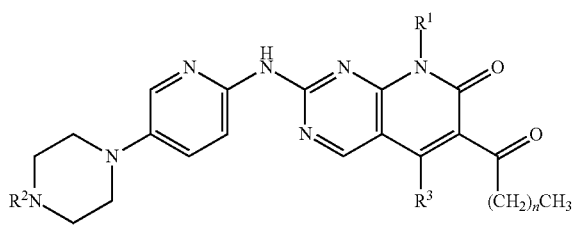

[2D]

In general formula 2[D]:

$R^1$ is hydrogen, aryl, $C_1$-$C_8$ alkyl, $C_1$-$C_8$ alkoxy, $C_3$-$C_7$ cycloalkyl, or $C_3$-$C_7$-heterocyclyl;

$R^2$ is selected from hydrogen, halogen, $C_1$-$C_8$ alkyl, $C_1$-$C_8$ acyl, $C_3$-$C_7$ cycloalkyl, $C_1$-$C_8$ alkoxy, $C_1$-$C_8$ alkoxyalkyl, $C_1$-$C_8$ haloalkyl, $C_1$-$C_8$ hydroxyalkyl, $C_2$-$C_8$ alkenyl, $C_2$-$C_8$ alkynyl, nitrile, nitro, $OR^5$, $SR^5$, $NR^5R^6$, $N(O)R^5R^6$, $P(O)(OR^5)(OR^6)$, $(CR^5R^6)_mNR^7R^8$, $COR^5$, $(CR^4R^5)_mC(O)R^7$, $CO_2R^5$, $CONR^5R^6$, $C(O)NR^5SO_2R^6$, $NR^5SO_2R^6$, $C(O)NR^5OR^6$, $S(O)_nR^5$, $SO_2NR^5R^6$, $P(O)(OR^5)(OR^6)$, $(CR^5R^6)_mP(O)(OR^7)(OR^8)$, $(CR^5R^6)_m$-aryl, $(CR^5R^6)_m$-heteroaryl, and $-CR^5=CR^6C(O)R^7$;

$R^3$ is, in each instance, independently, hydrogen, halogen, $C_1$-$C_6$ alkyl, $C_1$-$C_6$ haloalkyl, $C_1$-$C_6$ hydroxyalkyl, or $C_3$-$C_7$ cycloalkyl;

$R^5$, $R^6$, $R^7$, and $R^8$, are independently selected from hydrogen, $C_1$-$C_8$ alkyl, $C_2$-$C_8$ alkenyl, $C_2$-$C_8$ alkynyl, arylalkyl, cycloalkyl, heterocycloalkyl, aryl, heteroaryl, or heteroarylalkyl; m is from 0 to 6; and in the fatty acid moiety, n represents an integer from 9 to 20, and preferably is from 12-20.

Shown below as general formula [2E] is are examples of another preferred embodiment of the second class according to the present approach. In general formula [2E], $R^1$ is unsubstituted $C_5$-cycloalkyl, $R^2$ is H, $R^3$ is methyl, and n represents an integer from 9 to 20, and more preferably from 12-20.

A demonstrative embodiment of the second class is shown below formulas Compound [2F], in which $R^1$ is unsubstituted $C_5$-cycloalkyl (e.g., cyclopentyl), $R^2$ is H, $R^3$ is methyl, and n 12. As a result, this embodiment has a 14-carbon fatty acid (i.e., myristate) moiety.

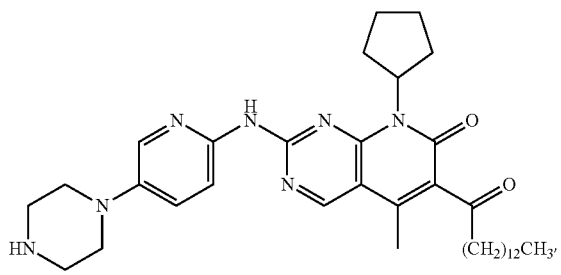

[2E]

[2F]

Table 2, below, summarizes results for various assays comparing Compound [2C] and its parent compound (Palbociclib), and contains the in vitro biological data for both compounds. The results show that Compound [2C] had a reduced potency in the 3D-mammosphere assay ($IC_{50}$ of about 5.1 vs. about 0.2 µM), when compared to the parent compound Palbociclib. However, Compound [2C] was non-toxic in the 2D-cell viability assay up to a concentration of 30 µM, whereas Palbociclib showed an $IC_{50}$ of about 0.1 µM. Further, Palbociclib was non-selective when comparing the 2D and 3D MCF7 assays. These results show that Compound [2C] demonstrates improved compound selectivity towards the 3D mammospheres, as opposed to normal cells. Thus, it should be appreciated that compounds of the present approach may be used for selectively targeting cancer cells and, in particular, CSCs. Both compounds where non-toxic against in the non-tumoral cell line hTERT-BJ1, up to the concentration of 90 µM, representing high selectivity towards the tumor cell line. Compounds in the second class of the present approach therefore show increased selectivity with respect to targeting cancer stem cells.

TABLE 2

Mammosphere assay results for demonstrative compound in second class.

| Compound | IC$_{50}$ (MCF7 mammosphere) | IC$_{50}$ (MCF7 monolayer) | SI (mammosphere/monolayer MCF7) | IC$_{50}$ (BJ1 monolayer) | SI (BJ1/MCF7 monolayer) |
|---|---|---|---|---|---|
| Palbociclib | 0.2 ± 0.2 μM | 0.1 ± 0.2 μM | Non-selective | >90 μM | >900 |
| Compound [2C] | 5.1 ± 1.0 μM | >30 μM | >5 | >90 μM | — |

Substituted Benzimidazole Compounds

A third class comprises substituted benzimidazole compounds having the general formula [3A], shown below. It should also be appreciated that pharmaceutically acceptable salts may also be used, such as those identified above, as would be understood by those having an ordinary level of skill in the art. It should be appreciated that some embodiments in the third class comprise derivatives of N-[5-[(4-ethylpiperazin-1-yl)methyl]pyridin-2-yl]-5-fluoro-4-(7-fluoro-2-methyl-3-propan-2-ylbenzimidazol-5-yl)pyrimidin-2-amine), also known as Abemaciclib. As with the compounds in the first two classes, compounds of the third class are also potent CDK 4/6 inhibitors.

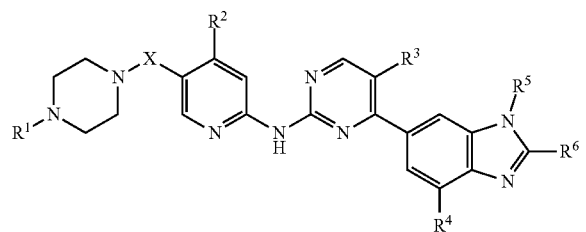

[3A]

In general formula 3A,

R$^1$ is a fatty acid moiety

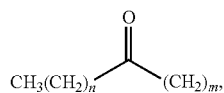

in which m is an integer from 0-4, and more preferably 0-2, such that when m is 0 there is a direct bond to the nitrogen in the piperazine, and n is an integer from 9-20, and more preferably from 12-20;

R$^2$ is H or C$_1$-C$_3$ alkyl;
R$^3$ and R$^4$ are H or fluorine, and at least one of R$^3$ and R$^4$ is fluorine;
R$^5$ is C$_3$-C$_5$ alkyl, C$_3$-C$_5$ cycloalkyl or cyclopropylmethyl;
R$^6$ is H or C$_1$-C$_3$ alkyl; and
X is a bond, C$_1$-C$_3$ alkyl, O, or S.

Shown below as general formula [3B] is a general formula for preferred embodiments of the third class according to the present approach. In general formula [3B], R$^1$ is s a fatty acid moiety

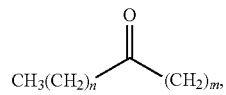

in which m is an integer from 0-4, and more preferably 0-2, such that when m is 0 there is a direct bond to the nitrogen in the piperazine, and n is an integer from 9-20, and more preferably from 12-20, R$^2$ is H, R$^3$ and R$^4$ are fluorine, R$^5$ is C$_3$ alkyl (isobutyl), and R$_6$ is methyl.

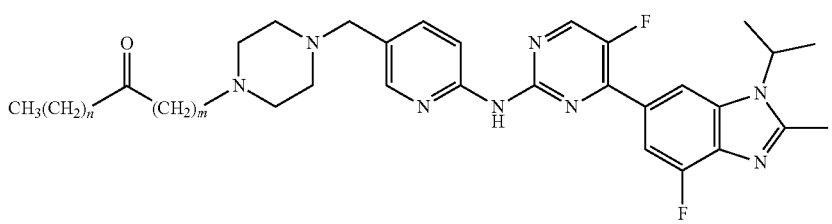

[3B]

Shown below as Compound [3C] is the formula for a demonstrative preferred embodiment of the third class according to the present approach. In general Compound [3C], R$^1$ is a fatty acid moiety

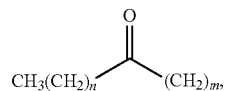

in which m is 0 and n is 12, R$^2$ is H, R$^3$ and R$^4$ are fluorine, R$^5$ is C$_3$ alkyl (isobutyl), and R$^6$ is methyl. Embodiments in which n is from 9 to 20 are contemplated, and planned for evaluation. The embodiment shown as Compound [3C] is a derivative of Abemaciclib, a CDK 4/6 inhibiting compound approved by the FDA for advanced and metastatic breast cancer treatment. Compound [3C], and other compounds having the formula [3A], are anticipated to be effective at inhibiting CDK 4/6, making them particularly suitable for use as an anti-cancer therapeutic and selectively targeting and inhibiting cancer cells and CSCs, as described herein.

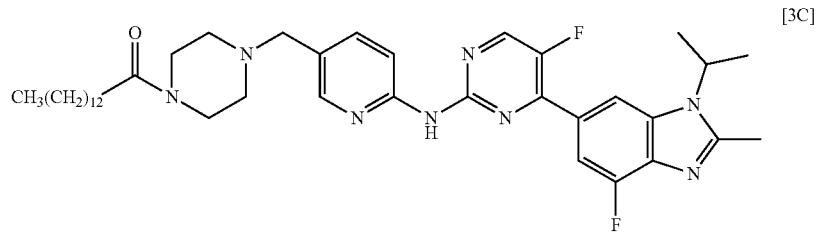

[3C]

A second demonstrative embodiment of the third class of compounds is shown below as formula 3D. In this example, $R^1$ is a fatty acid moiety

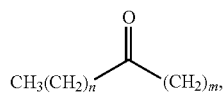

in which m is 2 and n is 12, $R^2$ is H, $R^3$ and $R^4$ are fluorine, $R^5$ is $C_3$ alkyl (isobutyl), and $R_6$ is methyl. As with compound [3C], this embodiment is expected to be more potent than Abemaciclib with respect to CDK 4/6 inhibition and selectivity, and is particularly suitable for use as an anti-cancer therapeutic as described herein.

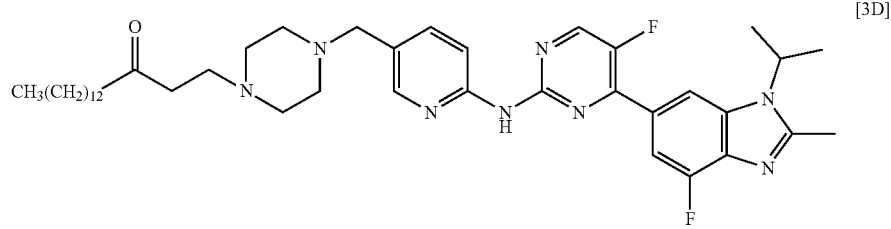

[3D]

Table 3 below shows the in vitro biological data for Abemaciclib. As can be seen, the compound is already highly potent in the 3D-mammosphere assay ($IC_{50}$ of <0.04 μM) prior to conjugation. Compounds having the formula [3A], including a variety of fatty acid moieties, are being evaluated. It should be appreciated from Table 3 that Abemaciclib is both highly specific and highly potent to CSCs. Thus, Abemaciclib may be used as a therapeutic agent to specifically target CSCs. Because of its selectivity, Abemaciclib may be used for treating and/or preventing tumor recurrence and/or metastasis, and for targeting circulating tumor cells.

TABLE 3

Mammosphere assay results for Abemaciclib.

| Compound | $IC_{50}$ (MCF7 mammo-sphere) | $IC_{50}$ (MCF7 monolayer) | SI (mammo-sphere/ monolayer MCF7) | $IC_{50}$ (BJ1 mono-layer) | SI (BJ1/MCF7 monolayer) |
|---|---|---|---|---|---|
| Abemaciclib | <0.04 μM | 11 μM | >50 | 30 ± 6 | 2.7 |

Figure 3:
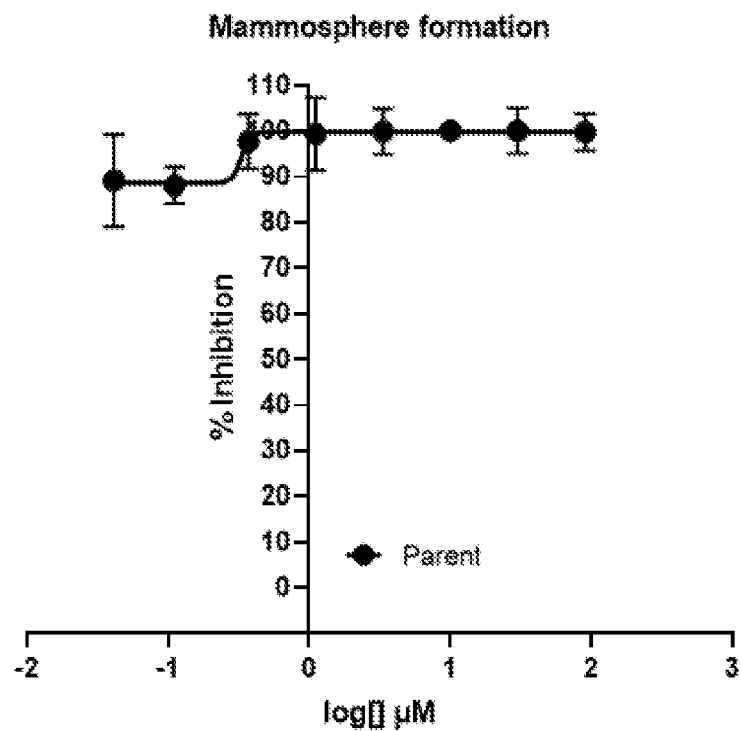
FIG. 3 is a dose-response curve for the parent compound of Compound [3C], using the mammosphere formation assay on the MCF7 cell line.
Figure 4:
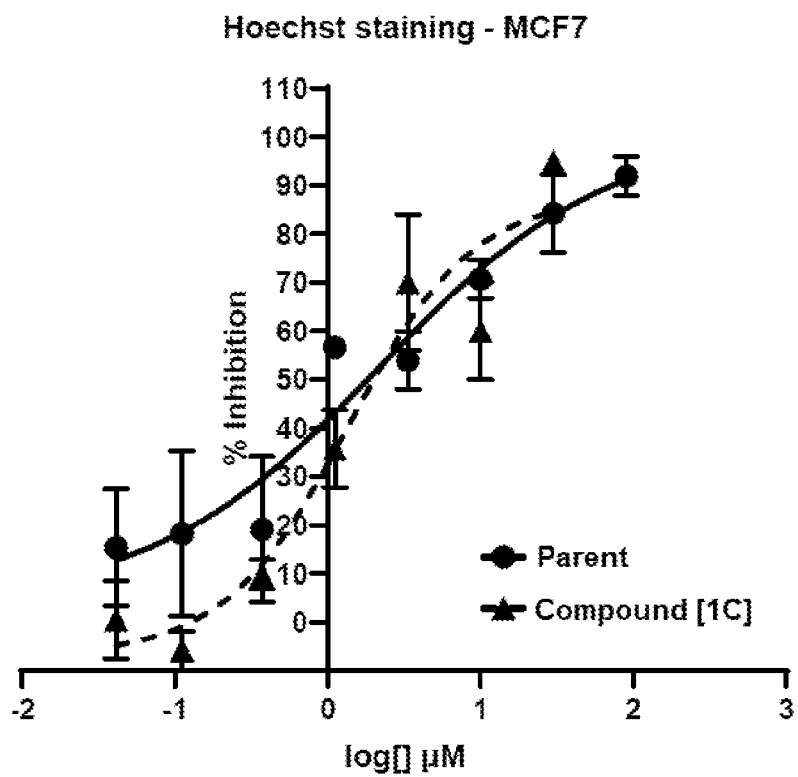
FIG. 4 shows dose-response curves comparing Compound [1C] to its parent compound, using the Hoechst staining assay on the MCF7 cell line.
Figure 5:
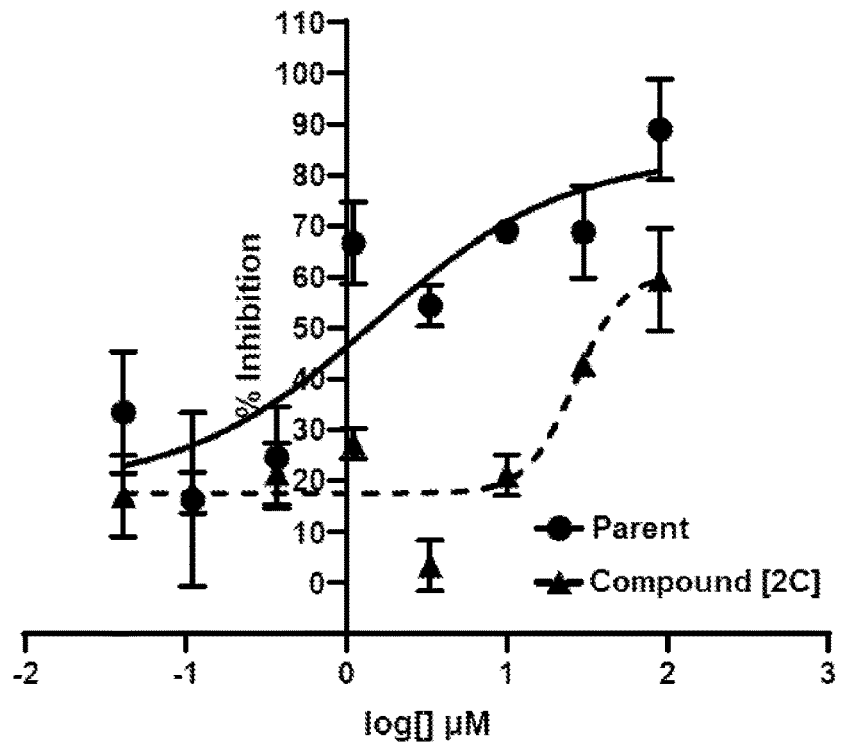
FIG. 5 shows dose-response curves comparing Compound [2C] to its parent compound, using the Hoechst staining assay on the MCF7 cell line.
Figure 6:
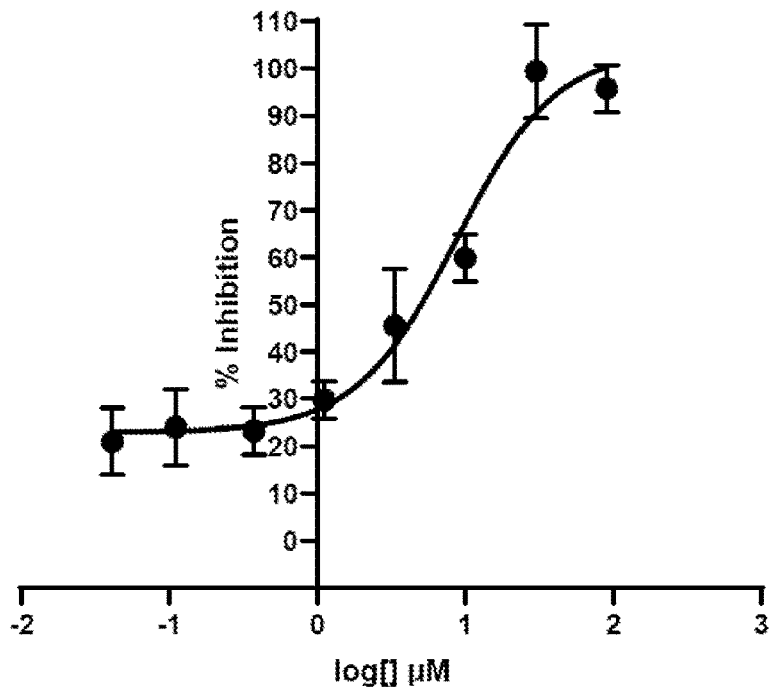
FIG. 6 is a dose-response curve comparing for the parent compound of Compound [3C], using the Hoechst staining assay on the MCF7 cell line.
Figure 7:
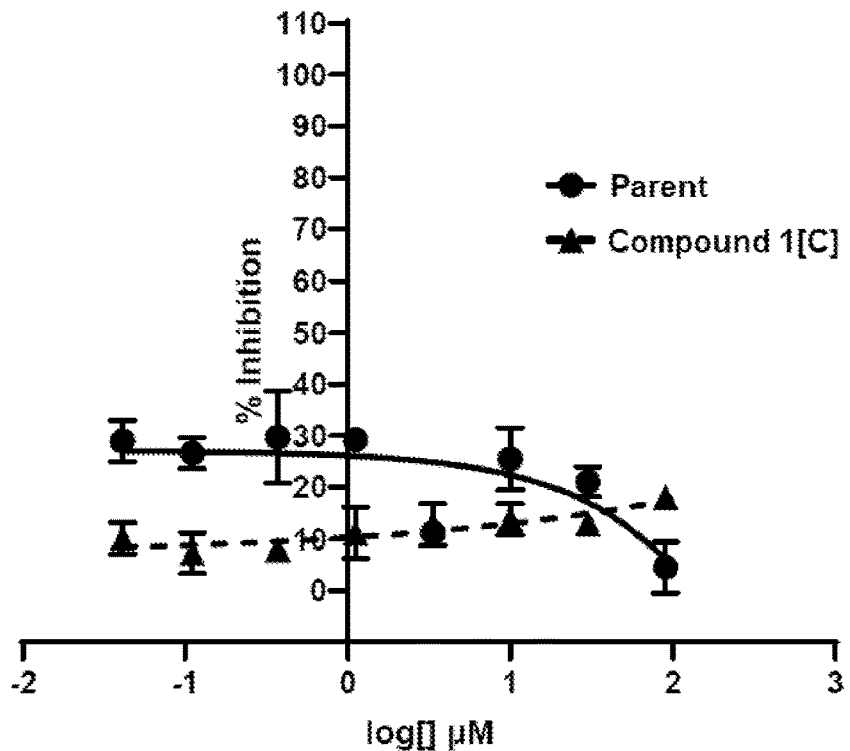
FIG. 7 shows dose-response curves comparing Compound [1C] to its parent compound, using the Hoechst staining assay on the hTERT-BJ1 cell line.
Figure 8:
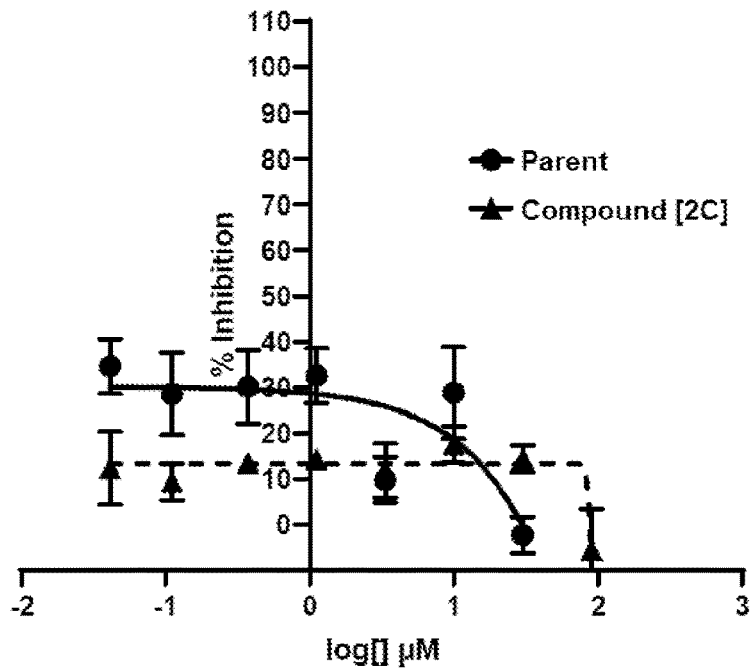
FIG. 8 shows dose-response curves comparing Compound [2C] to its parent compound, using the Hoechst staining assay on the hTERT-BJ1 cell line.
Figure 9:
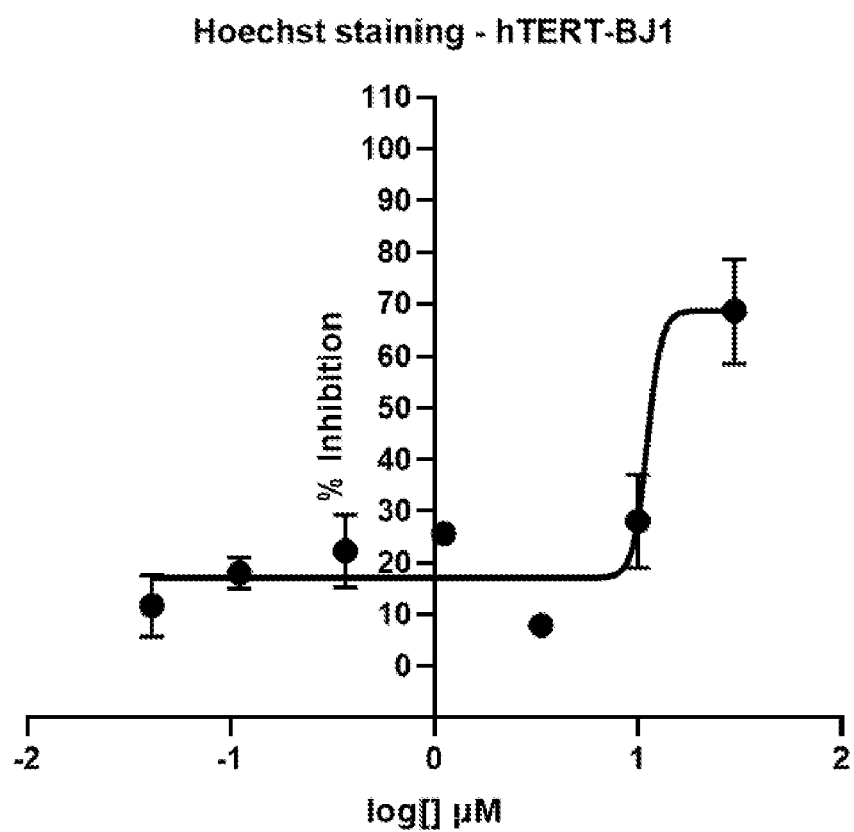
FIG. 9 is a dose-response curve comparing for the parent compound of Compound [3C], using the Hoechst staining assay on the hTERT-BJ1 cell line.

FIGS. 1-3 are dose-response curves for various compounds described herein, using the mammosphere assay. The assay was performed using the MCF7 cell line. The curves are plotted as a mean of two independent experiments, and the standard deviation for each point is represented by vertical bars. The inhibition percentage is shown as a function of the log of the concentration (μM). FIG. 1 shows dose-response curves comparing Compound [1C] to its parent compound, Ribociclib, using the mammosphere formation assay on the MCF7 cell line. FIG. 4 shows dose-response curves comparing Compound [1C] to its parent compound, using the Hoechst staining assay on the MCF7 cell line. As can be seen, Compound [1C] is more potent against MCF7 cells at each concentration. This demonstrates that compounds having the general formula [1A], and in particular general formula [1B], have efficacy as potent anti-cancer therapeutics. FIG. 7 shows dose-response curves comparing Compound [1C] to its parent compound, using the Hoechst staining assay on the hTERT-BJ1 cell line. The parent compound was more potent at most concentrations tested, demonstrating that compounds having the general formula [1A], and in particular general formula [1B], are more selective towards CSCs. Similar effects are expected for compounds having the general formula [1D].

Further, although the data disclosed herein relates to MCF7 and hTERT-BJ1 cell lines, the compounds of the present approach have efficacy for other types of cancer. In prior work, the inventors demonstrated that mitochondrial biogenesis inhibitors successfully inhibited tumor-sphere formation in a wide-variety of cell lines from several tumor types. Table 4, below, lists cancer cell lines that have been shown to be susceptible to mitochondrial biogenesis inhibitors. Given these results, the present approach is effective for numerous cancer types.

TABLE 4

Mitochondrial biogenesis inhibitors are effective against a wide variety of cancer types.

| Cancer Type | Cell Line(s) |
|---|---|
| Breast (ER+) | MCF7 |
|  | T47D |

TABLE 4-continued

Mitochondrial biogenesis inhibitors are effective against a wide variety of cancer types.

| Cancer Type | Cell Line(s) |
| --- | --- |
| Breast (ER−) | MDA-MB-231 |
| DAIC | MCF10.DCIS.com |
| DL | ("pre-malignant") |
| Ovarian | SKOV3 |
| | Tov21G |
| | ES2 |
| Prostate | PC3 |
| Pancreatic | MIA PaCa2 |
| Lung | A549 |
| Melanoma | A375 |
| Glioblastoma | U-87 MG |

The present approach describes pharmaceutical compositions comprising a therapeutically effective amount of a compound from the first class or the second class, or a pharmaceutically acceptable salt thereof, and a pharmaceutically acceptable carrier, diluent, or excipient therefor. Compounds according to the present approach may be used as anti-cancer therapeutics. Pharmaceutically-effective amounts of a compound in a pharmaceutically-acceptable carrier may be administered to a subject according to means known in the art. In some embodiments, a compound of the present approach may be used in conjunction with other cancer therapies, such as but not limited to chemotherapeutics, mitochondrial biogenesis inhibitors (e.g., mitoribos-cins, mitoketoscins, repurposcins such as antimitoscins), radiation therapy, phototherapy, and caloric restriction.

It should be appreciated that the person having an ordinary level of skill in the art can use methods common and known in the art to develop a formulation for a particular embodiment. In some embodiments, the pharmaceutical composition may be in a tablet, capsule, or pill. The pharmaceutical composition may have a dose of the therapeutic composition from 20 mg to 500 mg. In some embodiments, the pharmaceutical composition may comprise a tablet having 200 mg of the therapeutic compound, e.g., a compound described above, such as Compound [1C]. A tablet may contain a therapeutic compound content of at least about 35%, 40%, 45%, 50% or 55%, measured by w/w percentage of the therapeutic compound (as a free base) of the core tablet.

The tablet may have a core formed of microcrystalline cellulose, crospovidone type A, low-substituted hydroxypropylcellulose, magnesium stearate, colloidal anhydrous silica. In a first demonstrative embodiment, a tablet having 200 mg of the therapeutic compound (e.g., Compound [1C]) may include an inner core having microcrystalline cellulose (67.44 mg), hydroxypropyl cellulose (48.12 mg), crospovidone (29.20 mg), colloidal silicon dioxide (anhydrous) (2.12 mg), and magnesium stearate (6.36 mg), and an outer core having crospovidone (12.84 mg), colloidal silicon dioxide (anhydrous) (1.06 mg), and magnesium stearate (8.46 mg). In a second demonstrative embodiment, a tablet may have from about 10% to about 45% (w/w) of the therapeutic compound (e.g., Compound [2C]), and preferably about 18% to about 28% of the therapeutic compound; from about 4% to about 18% water-soluble acid; from about 20% to about 75% diluent; from about 5% to about 18% disintegrant; from about 0.2% to about 10% lubricant; and, optionally, glidant from about 0% to about 5%, and from about 0% to about 15% binder. It should be appreciated that pharmaceutical compositions of the present approach may closely resemble pharmaceutical compositions including the parent compound. For example, International Patent Application Publication WO 2016/166703, filed Apr. 14, 2016, describes examples of tablet formulations for Ribociclib, and is incorporated by reference in its entirety. As another example, International Patent Application Publication WO 2016/193860, filed May 24, 2016, describes solid dosage forms of Palbociclib, and is incorporated by reference in its entirety.

The tablet may have a film coating. The film coating may include iron oxide black, iron oxide red, soya lecithin, polyvinyl alcohol (partially hydrolysed), talc, titanium dioxide, and xanthan gum. The tablet may be coated using commercially available coating premixes, depending on the desired appearance of the final tablet. For example, persons having Opadry® (Colorcon, Harleysville, Pa.) is an HPMC (hydroxypropyl-methylcellulose) coating material and has the following composition: HPMC (Pharmacoat 603) 71.4%, polyethylene glycol 7.15%, talc 7.15%, and iron oxide 14.3%.

The selective inhibition of CDK 4/6 also indicates that the compounds described herein may be used to reduce or eliminate drug and/or therapy resistance in cancers. Because of their inhibitory activity against CDKs and other kinases, the compounds of the present approach are also useful research tools for studying the mechanism of action for such kinases, and may be used both in vitro and in vivo.

Methods of treatment described herein are preferably carried out by administering a therapeutically effective amount of a compound from either the first class or the second class, to a subject in need of treatment. The compounds are readily synthesized using the reactions steps as described below, or alternate reaction steps may be used. The alternate reaction steps would be readily recognized by one of skill in the art after reviewing this disclosure, and include the reaction steps described "Comprehensive Organic Synthesis", Trost, Fleming, Pergamon: 1991 and "Comprehensive organic Functional Group Transformations", Katritky, Meth-Cohn, Rees, Pergamon:1995, and can be administered by a variety of routes, including orally and parenterally, and have little or no toxicity.

The following abbreviations may be used in the following discussion of example synthesis methods: N-methylmorpholine (NMM), dichloromethane (DCM), dimethylformamide (DMF), ethylacetate (EtOAc), sodium hydrogen carbonate (NaHCO$_3$), sodium sulphate (Na$_2$SO$_4$), methanol (MeOH). In the description that follows, [M+H]$^+$ refers to the protonated molecule, and the identified value is the protonated molecule's mass. RT refers to the solute retention time.

Analytical LC-MS: Waters Sunfire C18 30×4.6 mm column, with a gradient eluent of 3-97% acetonitrile/water containing 0.05% formic acid. Time: 0-6 minutes. Preparative HPLC: LC Column: Phenomenex Kinetex 5 μm EVO C18 100 250×21.2 mm. Gradient eluent: 40-95% acetonitrile/water containing 0.1% formic acid.

In a first synthesis example, Compound [2C] shown above, also known as 6-acetyl-8-cyclopentyl-5-methyl-2-[[5-(4-tetradecanoylpiperazin-1-yl)-2-pyridyl]amino]pyrido[2,3-d]pyrimidin-7-one, was synthesized using Palbociclib (acquired from LC laboratories, Woburn, Mass., USA) Tetradecanoic acid (0.104 g, 0.46 mmol) was dissolved in thionyl chloride at room temperature. The solution was refluxed for 60 minutes, concentrated under reduced pressure and the residue was dissolved in dry DCM (2 ml) at room temperature to give 0.227 M stock solution of the acid chloride. The acid chloride stock solution (0.25 ml, 0.057 mmol) was added to a stirred mixture of 6-acetyl-8-cyclopentyl-5-methyl-2-[[5-(1-piperazinyl)-2-pyridinyl]amino]- pyrido[2,3-d]pyrimidin-7(8H)-one (0.024 g, 0.05 mmol) and NMM (18 µl, 0.16 mmol) in DCM (1 ml) and DMF (0.5 ml). The mixture was stirred at room temperature for 90 minutes. The solvents were evaporated under reduced pressure and the residue was dissolved in EtOAc (30 ml), washed with saturated NaHCO₃ (15 ml) and brine (15 ml), and then dried over Na₂SO₄. The drying agent was separated by filtration and filtrate was concentrated under reduced pressure to produce a crude product. The crude product was triturated with diethyl ether, and the resulting light brown solid was collected by filtration, washed with diethyl ether, and dried under vacuum to yield 6-acetyl-8-cyclopentyl-5-methyl-2-[[5-(4-tetradecanoylpiperazin-1-yl)-2-pyridyl]amino]pyrido[2,3-d]pyrimidin-7-one (0.0145 g). LC-MS 658.2 [M+H]⁺, RT 4.12 min.

In a second synthesis example, Compound [1C] shown above, also known as 7-cyclopentyl-N,N-dimethyl-2-[[5-(4-tetradecanoylpiperazin-1-yl)-2-pyridyl]amino]pyrrolo[2,3-d]pyrimidine-6-carboxamide, was synthesized using the same method as in the first synthesis example, except that instead of Palbociclib, Ribociclib (acquired from LC laboratories, Woburn, Mass., USA) (0,022 g, 0.05 mmol) was reacted with the acid chloride stock solution. The crude product was purified on silica gel (2-4% MeOH/DCM) to yield 7-cyclopentyl-N,N-dimethyl-2-[[5-(4-tetradecanoylpiperazin-1-yl)-2-pyridyl]amino]pyrrolo[2,3-d]pyrimidine-6-carboxamide (0.0166 g) as a light brown solid. LC-MS 645.2 [M+H]⁺, RT 2.72 min.

In a third synthesis example, Compound [3C] shown above, also known as 1-[4-[[6-[[5-fluoro-4-(7-fluoro-3-isopropyl-2-methyl-benzimidazol-5-yl)pyrimidin-2-yl]amino]-3-pyridyl]methyl]piperazin-1-yl]tetradecan-1-one, was synthesized from a series of intermediate compounds as follows. First, intermediate Compound [4A], shown below and known as tert-butyl 4-tetradecanoylpiperazine-1-carboxylate, was synthesized as follows. To a stirred solution of tetradecanoic acid (1.26 g, 5.5 mmol) and NMM (0.73 ml, 5.5 mmol) in dry DCM (20 ml) at room temperature under nitrogen atmosphere iso-butylchloroformate (0.65 ml, 5.0 mmol) was added. After 4 hours a solution of 1-Boc-piperazine (0.93 g, 5.0 mmol) in dry DCM (5 ml) was added to the mixture. The mixture was stirred for 16 hours. The solvent was removed under reduced pressure to yield a crude product. The crude product was dissolved in EtOAc (75 ml), washed with 2M HCl (50 ml), saturated NaHCO₃ (40 ml), and brine (30 ml), and then dried over MgSO₄. After filtration the solvent was evaporated under reduced pressure to yield tert-Butyl 4-tetradecanoylpiperazine-1-carboxylate (1.76 g) as a white solid. LC-MS 397.2 [M+H]⁺, RT 4.02 min.

[4A]

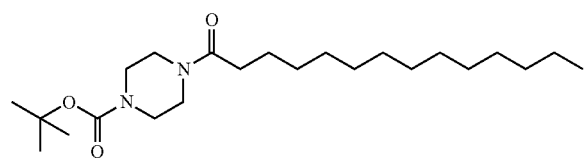

Second, intermediate Compound [4B], shown below and known as 1-piperazin-1-yltetradecan-1-one was synthesized as follows. A solution of tert-Butyl 4-tetradecanoylpiperazine-1-carboxylate (0.51 g, 1.26 mmol) in a 1:1 mixture of dry DCM (10 ml) and trifluoroacetic acid, or TFA (10 ml), was stirred at room temperature under nitrogen atmosphere for 90 minutes, the solvent was removed under reduced pressure to yield a crude product. The crude product was dissolved in EtOAc (30 ml), washed with saturated NaHCO₃ (15 ml), and brine (15 ml), and dried over MgSO₄. After filtration the solvent was evaporated under reduced pressure to yield 1-piperazin-1-yltetradecan-1-one (0.33 g) as a white waxy solid. LC-MS 297.3 [M+H]⁺, RT 1.81 min.

[4B]

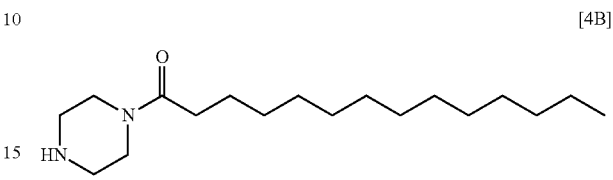

Third, intermediate Compound [4C], shown below and known as 6-[[5-fluoro-4-(7-fluoro-3-isopropyl-2-methyl-benzimidazol-5-yl)pyrimidin-2-yl]amino]pyridine-3-carbaldehyde, was prepared as follows. A suspension of 6-amino-pyridine-3-carbaldehyde (0.076 g, 0.625 mmol), 6-(2-chloro-5-fluoro-pyrimidin-4-yl)-4-fluoro-1-isopropyl-2-methyl-benzimidazole (0.161 g, 0.500 mmol), Xantphos (0.0276 g, 0.0476 mmol), palladium chloride (0.0056 g, 0.0315 mmol) and K2CO₃ (0.069 g, 0.500 mmol) in 2-methyl-2-butanol (4 ml) was heated in a sealed tube at +100° C. for 18 hours. The reaction mixture was cooled to room temperature, diluted with EtOAc (30 ml) and water (30 ml). The precipitate with the aqueous phase was separated and collected by filtration. The light brown solid was washed with water (30 ml) and acetone (20 ml), and dried under vacuum to yield 6-[[5-fluoro-4-(7-fluoro-3-isopropyl-2-methyl-benzimidazol-5-yl)pyrimidin-2-yl]amino]pyridine-3-carbaldehyde (0.125 g) as a light brown solid. LC-MS 409.0 [M+H]⁺, RT 2.07 min.

[4C]

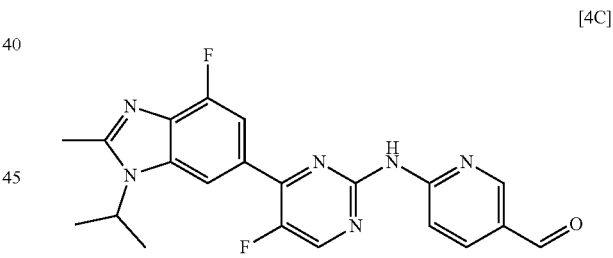

Fourth, the intermediate Compound [4D], shown below and known as 1-[4-[[6-[[5-fluoro-4-(7-fluoro-3-isopropyl-2-methyl-benzimidazol-5-yl)pyrimidin-2-yl]amino]-3-pyridyl]-methyl]piperazin-1-yl]tetradecan-1-one, also shown above as Compound [3C], was synthesized as follows. A suspension of 6-[[5-fluoro-4-(7-fluoro-3-isopropyl-2-methyl-benzimidazol-5-yl)pyrimidin-2-yl]amino]pyridine-3-carbaldehyde (0.050 g, 0.122 mmol), 1-piperazin-1-yltetradecan-1-one (0.030 g, 0.100 mmol) and sodium triacetoxyborohydride (0.212 g, 1.00 mmol) in DCE (20 ml) was heated in a sealed tube at +60° C. for 90 minutes. The reaction mixture was cooled to room temperature diluted with DCM (30 ml), washed with water (10 ml), and brine (10 ml), and dried over MgSO₄. After filtration the solvent was evaporated under reduced pressure to yield a crude product (0.1564 g) which was purified by the preparative HPLC to yield 1-[4-[[6-[[5-fluoro-4-(7-fluoro-3-isopropyl-2-methyl-benzimidazol-5-yl)pyrimidin-2-yl]amino]-3- pyridyl]methyl]piperazin-1-yl]tetradecan-1-one (0.012 mg). LC-MS 689.2 [M+H]$^+$, RT 2.44 min

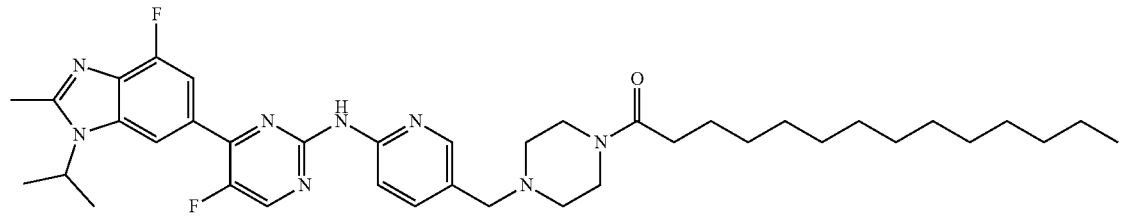

[4D]

The following paragraphs describe the materials and methods used in connection with the data and embodiments set forth herein. It should be appreciated that those having an ordinary level of skill in the art may use alternative materials and methods generally accepted in the art, without deviating from the present approach.

With respect to cell culture and reagents, the human breast adenocarcinoma cell line (MCF-7) was from the American Type Culture Collection (ATCC). hTERT-BJ1 cells were from Clontech, Inc. MCF-7 and hTERT-BJ1 cells were grown in DMEM supplemented with 10% fetal bovine serum, GlutaMAX and 1% penicillin-streptomycin and incubated at 37 C in a humidified 5% $CO_2$ incubator. The medium was changed 2-3 times/week.

Mammosphere formation assay: A single cell suspension was prepared using enzymatic (1× Trypsin-EDTA, Sigma Aldrich, cat. #T3924), and manual disaggregation (25 gauge needle). Five thousand cells were plated with in mammosphere medium (DMEM-F12/B27/20 ng/ml EGF/PenStrep), under non-adherent conditions, in six wells plates coated with 2-hydroxyethylmethacrylate (poly-HEMA, Sigma, cat. #P3932). Cells were grown for 5 days and maintained in a humidified incubator at 37° C. at an atmospheric pressure in 5% (v/v) carbon dioxide/air. After 5 days, 3D spheroids with a diameter greater than 50 µm were counted using a microscope, fitted with a graticule eye-piece, and the percentage of cells which formed spheroids was calculated and normalized to one (1=100% MFE; mammosphere forming efficiency). Mammosphere assays were performed in triplicate and repeated three times independently.

A Hoechst-based viability assay was used to characterize the selectivity of compounds according to the present approach, for the preferential targeting of cancer cells. Briefly, MCF7 cell monolayers were treated with a compound at concentrations ranging from 1 µM to 100 µM, for a period of one day. Cell viability was assessed using Hoechst 33342, a nuclear dye that stains DNA in live cells. The viability of normal human fibroblasts (hTERT-BJ1) treated with the compounds described herein was also assessed in parallel. Quantitation was performed with a plate-reader.

The terminology used in the description of embodiments of the present approach is for the purpose of describing particular embodiments only and is not intended to be limiting. As used in the description and the appended claims, the singular forms "a," "an" and "the" are intended to include the plural forms as well, unless the context clearly indicates otherwise. The present approach encompasses numerous alternatives, modifications, and equivalents as will become apparent from consideration of the following detailed description.

It will be understood that although the terms "first," "second," "third," "a)," "b)," and "c)," etc. may be used herein to describe various elements of the present approach, and the claims should not be limited by these terms. These terms are only used to distinguish one element of the present approach from another. Thus, a first element discussed below could be termed an element aspect, and similarly, a third without departing from the teachings of the present approach. Thus, the terms "first," "second," "third," "a)," "b)," and "c)," etc. are not intended to necessarily convey a sequence or other hierarchy to the associated elements but are used for identification purposes only. The sequence of operations (or steps) is not limited to the order presented in the claims.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. All publications, patent applications, patents and other references mentioned herein are incorporated by reference in their entirety. In case of a conflict in terminology, the present specification is controlling.

Also, as used herein, "and/or" refers to and encompasses any and all possible combinations of one or more of the associated listed items, as well as the lack of combinations when interpreted in the alternative ("or").

Unless the context indicates otherwise, it is specifically intended that the various features of the present approach described herein can be used in any combination. Moreover, the present approach also contemplates that in some embodiments, any feature or combination of features described with respect to demonstrative embodiments can be excluded or omitted.

As used herein, the transitional phrase "consisting essentially of" (and grammatical variants) is to be interpreted as encompassing the recited materials or steps "and those that do not materially affect the basic and novel characteristic(s)" of the claim. Thus, the term "consisting essentially of" as used herein should not be interpreted as equivalent to "comprising."

Having thus described certain embodiments of the present approach, it is to be understood that the scope of the appended claims is not to be limited by particular details set forth in the above description as many apparent variations thereof are possible without departing from the spirit or scope thereof as hereinafter claimed.

What is claimed is:

1. A compound of the general formula

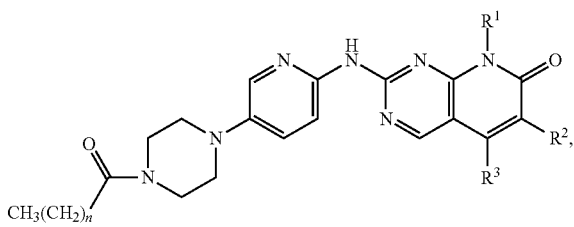

in which:
- $R^1$ is hydrogen, aryl, $C_1$-$C_8$ alkyl, $C_1$-$C_8$ alkoxy, $C_3$-$C_7$ cycloalkyl, or $C_3$-$C_7$-heterocyclyl;
- $R^2$ is independently selected from hydrogen, halogen, $C_1$-$C_8$ alkyl, $C_1$-$C_8$ acyl, $C_3$-$C_7$ cycloalkyl, $C_1$-$C_8$ alkoxy, $C_1$-$C_8$ alkoxyalkyl, $C_1$-$C_8$ haloalkyl, $C_1$-$C_8$ hydroxyalkyl, $C_2$-$C_8$ alkenyl, $C_2$-$C_8$ alkynyl, nitrile, nitro, $OR^5$, $SR^5$, $NR^5R^6$, $N(O)R^5R^6$, $P(O)(OR^5)(OR^6)$, $(CR^5R^6)_m NR^7R^8$, $COR^5$, $(CR^4R^5)_m C(O)R^7$, $CO_2R^5$, $CONR^5R^6$, $C(O)NR^5SO_2R^6$, $NR^5SO_2R^6$, $C(O)NR^5OR^6$, $S(O)_n R^5$, $SO_2NR^5R^6$, $P(O)(OR^5)(OR^6)$, $(CR^5R^6)_m P(O)(OR^7)(OR^8)$, $(CR^5R^6)_m$-aryl, $(CR^5R^6)_m$-heteroaryl, and —$CR^5$=$CR^6C(O)R^7$;
- $R^3$ is independently selected from hydrogen, halogen, $C_1$-$C_6$ alkyl, $C_1$-$C_6$ haloalkyl, $C_1$-$C_6$ hydroxyalkyl, or $C_3$-$C_7$ cycloalkyl;
- $R^5$, $R^6$, $R^7$, and $R^8$, are independently hydrogen, $C_1$-$C_8$ alkyl, $C_2$-$C_8$ alkenyl, $C_2$-$C_8$ alkynyl, arylalkyl, cycloalkyl, heterocycloalkyl, aryl, heteroaryl, or heteroarylalkyl; m is from 0 to 6; and
- n represents an integer from 9 to 20.

2. The compound of claim 1, wherein n is an integer from 12 to 20.

3. The compound of claim 2, wherein $R^1$ is cyclopentyl, and $R^2$ is acetyl.

4. The compound of claim 1, wherein the compound is

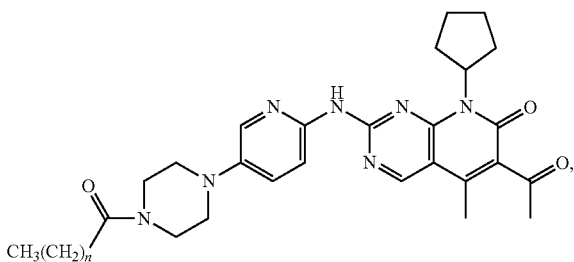

in which n represents an integer from 9 to 20.

5. The compound of claim 4, in which n is an integer from 12 to 20.

6. The compound of claim 4, in which n is 12.

7. A pharmaceutical composition comprising a compound of claim 1, or a pharmaceutically acceptable salt thereof, and a pharmaceutically acceptable carrier.

8. The pharmaceutical composition of claim 7, wherein the composition is a tablet comprising a core having between 18% and 55% by weight of the compound of any of claims 1 to 6, and a pharmaceutically acceptable carrier.

9. The pharmaceutical composition of claim 8, wherein the pharmaceutically acceptable carrier comprises microcrystalline cellulose, crospovidone type A, low-substituted hydroxypropylcellulose, magnesium stearate, and colloidal anhydrous silica.

10. A method for treating cancer, the method comprising administering to a patient in need thereof, a pharmaceutically effective amount of the compound of claim 1 or the pharmaceutical composition of claim 7.

11. A method for treating or preventing metastatic diseases, the method comprising administering to a patient in need thereof, a pharmaceutically effective amount of the compound of claim 1 or the pharmaceutical composition of claim 7.

12. A method for treating or preventing tumor recurrence, the method comprising administering to a patient in need thereof, a pharmaceutically effective amount of the compound of claim 1 or the pharmaceutical composition of claim 7.

13. A method for reducing treatment resistance of a cancer, the method comprising administering to a patient in need thereof, a pharmaceutically effective amount of the compound of claim 1 or the pharmaceutical composition of claim 7.

14. A method for treating or preventing at least one of radiation therapy resistance, chemotherapy resistance and hormone therapy resistance, the method comprising administering to a patient in need thereof, a pharmaceutically effective amount of the compound of claim 1 or the pharmaceutical composition of claim 7.

15. A method for preventing or reducing the proliferation of at least one of cancer cells, cancer stem cells, and circulating tumor cells, the method comprising administering to a patient in need thereof, a pharmaceutically effective amount of the compound of claim 1 or the pharmaceutical composition of claim 7.

* * * * *